(12) United States Patent
Ren et al.

(10) Patent No.: US 11,938,475 B2
(45) Date of Patent: Mar. 26, 2024

(54) FLOW CELLS WITH HYDROGEL COATING

(71) Applicants: ILLUMINA, INC., San Diego, CA (US); ILLUMINA CAMBRIDGE LIMITED, Cambridge (GB)

(72) Inventors: Hongji Ren, San Diego, CA (US); Jonathan Mark Boutell, Bishops Stortford (GB); John A. Moon, San Diego, CA (US); M. Shane Bowen, Encinitas, CA (US); Alex Nemiroski, San Diego, CA (US); Gary Mark Skinner, Kedington (GB); Kenny Chen, San Diego, CA (US)

(73) Assignees: Ilumina, Inc., San Diego, CA (US); Illumina Cambridge Limited, Cambridge (GB)

(*) Notice: Subject to any disclaimer, the term of this patent is extended or adjusted under 35 U.S.C. 154(b) by 734 days.

(21) Appl. No.: 17/114,134

(22) Filed: Dec. 7, 2020

(65) Prior Publication Data

US 2021/0086174 A1  Mar. 25, 2021

Related U.S. Application Data

(62) Division of application No. 16/626,393, filed as application No. PCT/US2018/066011 on Dec. 17, 2018, now Pat. No. 10,919,033.

(Continued)

(51) Int. Cl.
*B01L 3/00* (2006.01)
*B01J 19/00* (2006.01)
(Continued)

(52) U.S. Cl.
CPC .......... *B01L 3/502* (2013.01); *B01J 19/0046* (2013.01); *C08F 220/56* (2013.01);
(Continued)

(58) Field of Classification Search
None
See application file for complete search history.

(56) References Cited

U.S. PATENT DOCUMENTS 8,603,791 B2  12/2013  Krishnan et al.
8,778,848 B2   7/2014  Lin et al.
(Continued)

FOREIGN PATENT DOCUMENTS

CN  101528979 A   9/2009
CN  107108822 A   8/2017
(Continued)

OTHER PUBLICATIONS

Annabi, N., et al., "Hydrogel-Coated Microfluidic Channels for Cardiomyocyte Culture", Lab on a Chip, 2013, pp. 3569-3577.

*Primary Examiner* — David P Turocy
(74) *Attorney, Agent, or Firm* — Dierker & Kavanaugh, P.C.

(57) ABSTRACT

In an example of the method, a functionalized coating layer is applied in depressions of a patterned flow cell substrate. The depressions are separated by interstitial regions. A primer is grafted to the functionalized coating layer to form a grafted functionalized coating layer in the depressions. A hydrogel is applied on at least the grafted functionalized coating layer.

7 Claims, 7 Drawing Sheets

Related U.S. Application Data

(60) Provisional application No. 62/609,105, filed on Dec. 21, 2017.

(51) Int. Cl.

| | | |
|---|---|---|
| *C08F 220/56* | (2006.01) | |
| *C08F 220/60* | (2006.01) | |
| *C09D 133/26* | (2006.01) | |
| *C12Q 1/6876* | (2018.01) | |

(52) U.S. Cl.
CPC ........ *C08F 220/603* (2020.02); *C09D 133/26* (2013.01); *C12Q 1/6876* (2013.01); *B01J 2219/00475* (2013.01); *B01J 2219/00729* (2013.01); *B01L 2200/12* (2013.01); *B01L 2300/0893* (2013.01); *B01L 2300/16* (2013.01)

(56) References Cited

U.S. PATENT DOCUMENTS

| | | |
|---|---|---|
| 8,822,346 B1 | 9/2014 | Weiner |
| 10,619,204 B2 | 4/2020 | Gunderson et al. |
| 2009/0093064 A1 | 4/2009 | Kolesnychenko |
| 2009/0209436 A1 | 8/2009 | Larman et al. |
| 2009/0247414 A1 | 10/2009 | Obradovic et al. |
| 2010/0120630 A1 | 5/2010 | Huang et al. |
| 2010/0284859 A1 | 11/2010 | Cooney et al. |
| 2011/0059865 A1 | 3/2011 | Smith et al. |
| 2012/0252686 A1 | 10/2012 | Umbarger et al. |
| 2014/0243224 A1 | 8/2014 | Barnard et al. |
| 2015/0005447 A1 | 1/2015 | Berti et al. |
| 2015/0175948 A1 | 6/2015 | Yamamoto |
| 2016/0215324 A1 | 7/2016 | Srinivasan et al. |
| 2016/0246170 A1 | 8/2016 | Bowen et al. |
| 2017/0342487 A1 | 11/2017 | George et al. |
| 2018/0327832 A1 | 11/2018 | Ramirez et al. |

FOREIGN PATENT DOCUMENTS

| | | | | |
|---|---|---|---|---|
| JP | 2004194652 A | 7/2004 | | |
| KR | 1020070088979 A | 8/2007 | | |
| RU | 2008144969 A | 5/2010 | | |
| WO | 2006/078470 A2 | 7/2006 | | |
| WO | WO-2013063382 A2 * | 5/2013 | .......... | B01J 19/0046 |
| WO | 2015/100373 A2 | 7/2015 | | |
| WO | 2016/075204 A1 | 5/2016 | | |
| WO | WO-2016075204 A1 * | 5/2016 | .......... | B01J 19/0046 |
| WO | 2016/151719 A1 | 9/2016 | | |
| WO | 2017015018 A1 | 1/2017 | | |
| WO | 2017/201198 A1 | 11/2017 | | |
| WO | 2018/208561 A1 | 11/2018 | | |

\* cited by examiner

To Fig 3E     To Fig 3H

From Fig. 3D

FLOW CELLS WITH HYDROGEL COATING

CROSS-REFERENCE TO RELATED APPLICATIONS

This application is a divisional application of U.S. Ser. No. 16/626,393, filed Dec. 24, 2019, which itself is a national stage entry under 35 U.S.C. § 371 of International application No. PCT/US2018/066011, filed Dec. 17, 2018, which itself claims the benefit of U.S. Provisional Application Ser. No. 62/609,105, filed Dec. 21, 2017, the content of each of which is incorporated by reference herein in its entirety.

BACKGROUND

Biological arrays are among a wide range of tools used to detect and analyze molecules, including deoxyribonucleic acid (DNA) and ribonucleic acid (RNA). In these applications, the arrays are engineered to include probes for nucleotide sequences present in genes of humans and other organisms. In certain applications, for example, individual DNA and RNA probes may be attached at locations in a geometric grid (or randomly) on an array support. A test sample, e.g., from a person or organism, may be exposed to the grid, such that complementary fragments hybridize to the probes at the individual sites in the array. The array can then be examined by scanning specific frequencies of light over the sites to identify which fragments are present in the sample, by fluorescence of the sites at which the fragments hybridized.

Biological arrays may be used for genetic sequencing. In general, genetic sequencing involves determining the order of nucleotides or nucleic acids in a length of genetic material, such as a fragment of DNA or RNA. Increasingly longer sequences of base pairs are being analyzed, and the resulting sequence information may be used in various bioinformatics methods to logically fit fragments together so as to reliably determine the sequence of extensive lengths of genetic material from which the fragments were derived. Automated, computer-based examination of characteristic fragments have been developed, and have been used in genome mapping, identification of genes and their function, evaluation of risks of certain conditions and disease states, and so forth. Beyond these applications, biological arrays may be used for the detection and evaluation of a wide range of molecules, families of molecules, genetic expression levels, single nucleotide polymorphisms, and genotyping.

INTRODUCTION

In a first aspect, a method comprises applying a functionalized coating layer in depressions of a patterned flow cell substrate, wherein the depressions are separated by interstitial regions; grafting a primer to the functionalized coating layer to form a grafted functionalized coating layer in the depressions; and applying a hydrogel on the grafted functionalized coating layer.

In an example of this first aspect of the method, the hydrogel is selected from the group consisting of a poly(N-(5-azidoacetamidylpentyl) acrylamide-co-acrylamide), crosslinked polyacrylamide, an agarose gel, and crosslinked polyethylene glycol.

In an example of this first aspect of the method, the hydrogel is disposed on the grafted functionalized coating layer. In one example, the hydrogel is applied on the functionalized coating layer in the depressions and on at least some of the interstitial regions. In another example, applying the hydrogel includes selectively depositing the hydrogel on the grafted functionalized coating layer in the depressions.

In an example of this first aspect of the method, prior to applying the functionalized coating layer, the method further comprises treating a surface of the patterned flow cell substrate to attach a functional group to the surface to form treated depressions and treated interstitial regions. In this example, applying the functionalized coating layer in the depressions includes: applying the functionalized coating layer in the treated depressions and on the treated interstitial regions; and polishing the functionalized coating layer from the treated interstitial regions.

In an example of this first aspect of the method, applying the hydrogel involves applying an aqueous mixture including from about 0.001% up to about 0.1% (mass to volume) of a hydrogel material. In an example, the hydrogel material is selected from the group consisting of a poly(N-(5-azidoacetamidylpentyl) acrylamide-co-acrylamide), crosslinked polyacrylamide, an agarose gel, and crosslinked polyethylene glycol.

In an example of this first aspect of the method, a perimeter of the patterned flow cell substrate has a spacer layer bonded thereto, and after the hydrogel is applied, the method further comprises bonding a lid to the spacer layer.

In an example of this first aspect of the method, after the functionalized coating layer is applied and before the primer is grafted, the method further comprises bonding a lid to at least some of the interstitial regions.

In an example of this first aspect of the method, applying the hydrogel includes selectively depositing the hydrogel on the grafted functionalized coating layer. It is to be understood that any features of this first aspect of the method may be combined together in any desirable manner and/or configuration.

In a second aspect, a method comprises attaching a silane or a silane derivative to a surface of a patterned substrate including a flow channel having depressions defined therein, wherein the depressions are separated by interstitial regions, thereby forming silanized depressions and silanized interstitial regions; applying a functionalized coating layer in the silanized depressions and on the silanized interstitial regions; polishing the functionalized coating layer from the silanized interstitial regions; grafting a primer to the functionalized coating layer in the silanized depressions to form a grafted functionalized coating layer in the depressions; and applying a hydrogel on the grafted functionalized coating layer in the depressions.

In an example of this second aspect, applying the hydrogel involves applying an aqueous mixture including from about 0.001% up to about 0.1% (mass to volume) of a hydrogel material. In this example, the hydrogel material is selected from the group consisting of a poly(N-(5-azidoacetamidylpentyl) acrylamide-co-acrylamide), crosslinked polyacrylamide, an agarose gel, and crosslinked polyethylene glycol.

In an example of this second aspect, a spacer layer is bonded to the patterned substrate and defines a perimeter of the flow channel; and after the hydrogel is applied, the method further comprises bonding a lid to the spacer layer.

In an example of this second aspect, after the functionalized coating layer is polished and before the primer is grafted, the method further comprises bonding a lid to at least some of the interstitial regions.

In an example of this second aspect of the method, applying the hydrogel includes applying the hydrogel on the grafted functionalized coating layer in the depressions. In one example, the hydrogel is applied on the functionalized coating layer in the depressions and on at least some of the interstitial regions. In another example, applying the hydrogel includes selectively depositing the hydrogel on the grafted functionalized coating layer.

It is to be understood that any features of this second aspect of the method may be combined together in any desirable manner. Moreover, it is to be understood that any combination of features of this aspect of the method and/or of the first aspect of the method may be used together, and/or that any features from either or both of these aspects may be combined with any of the examples disclosed herein.

In another aspect, a flow cell comprises a patterned substrate including depressions separated by interstitial regions; sequencing surface chemistry attached to each of the depressions, the sequencing surface chemistry including: a functionalized coating layer; and a primer grafted to the functional coating layer; and a hydrogel on the sequencing surface chemistry and optionally on some of the interstitial regions.

In an example of the flow cell, the hydrogel is also on at least some of the interstitial regions.

In an example of the flow cell, the functionalized coating layer is poly(N-(5-azidoacetamidylpentyl)acrylamide-co-acrylamide).

In an example of the flow cell, the hydrogel is selected from the group consisting of a poly(N-(5-azidoacetamidylpentyl) acrylamide-co-acrylamide), crosslinked polyacrylamide, an agarose gel, and crosslinked polyethylene glycol.

In an example of the flow cell, the hydrogel is not grafted to the surface chemistry.

In an example of the flow cell, the patterned substrate includes at least one flow channel; the depressions are defined in the at least one flow channel; and the flow cell further comprises a spacer layer attached to other interstitial regions of the patterned substrate such that the spacer layer defines a perimeter of the at least one flow channel. In this example, the flow cell may further comprise a lid attached to the spacer layer.

It is to be understood that any features of this aspect of the flow cell may be combined together in any desirable manner. Moreover, it is to be understood that any combination of features of this aspect of the flow cell and/or of the first and/or second aspects of the method may be used together, and/or that any features from any of aspects may be combined with any of the examples disclosed herein.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear.

DETAILED DESCRIPTION

Figure 1:
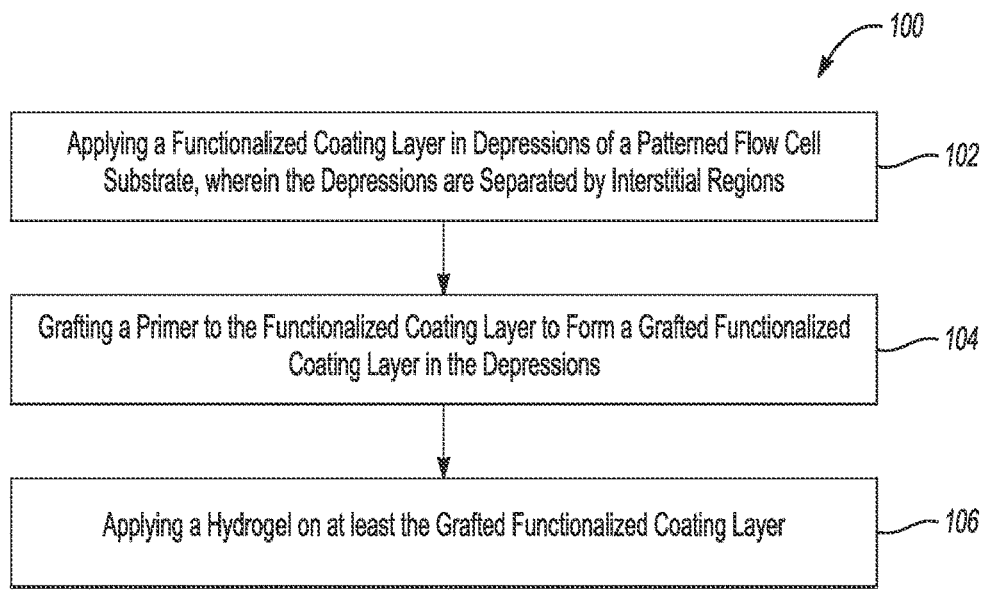
FIG. 1 is a flow diagram illustrating an example of a method disclosed herein.

Flow cells are often used in sequencing operations, assays, and other biological applications. Patterned flow cells may include a substrate or support in which or on which depressions are defined; and chemically and/or biologically active surface chemistry may be confined to the depressions. As an example, the surface chemistry includes a functionalized coating layer and a primer. In some sequencing operations, after the primer is immobilized in the depressions of the flow cell substrate, a sequencing template (including a portion that is complementary to the primer) may be introduced into the depressions, and then the sequencing template may be amplified to create identical copies of the sequencing template (the process of which is referred to herein as cluster generation).

In the examples disclosed herein, a hydrogel (also referred to herein as a hydrogel coating) is included directly on the surface chemistry, i.e., on the functionalized coating layer and the primer. It has been found that the hydrogel coating can slow down the sequencing template seeding speed at the time of cluster generation. As a result, after one sequencing template is seeded in the depression, there is more time (as compared to when the hydrogel is not included) to amplify the template into larger clusters, before any subsequent sequencing template has a chance to diffuse through the hydrogel and into the depression. This increases the population of depressions that seeds a single sequencing template. In other words, this increases monoclonal clustering (i.e., the creation of multiple copies of one type of sequencing template) within a particular depression, and reduces polyclonal clustering (i.e., the creation of multiple copies of multiple types of sequencing templates) within a particular depression. The number of clusters passing filter after duplicate removal may be indicative of increased monoclonal clustering. In an example, the net PF % for examples disclosed herein including the hydrogel coating ranges from about 2% to about 17% higher than the net PF % for comparative examples that do not include the hydrogel coating.

The method(s) disclosed herein may be performed entirely at the wafer level, entirely at the die level, in part at the wafer level, and/or in part at the die level. As an example of performing the method partially at the wafer and die levels, the method may be initiated using a wafer, which is then diced to form several dies, and the method may continue using each of the dies. The ability to perform open wafer processing, at least in some examples, enables a variety of metrology/analytical techniques to be used for quality control and characterization. Prior to being bonded to form a flow cell, the patterned and surface modified wafer/substrate may be exposed to, for example, atomic force microscopy (AFM), scanning electron microscopy (SEM), ellipsometry, goniometry, scatterometry, and/or fluorescence techniques. Alternatively, the bonded flow cell may be exposed to these techniques. At the die level, the method(s) may be performed on an open faced die, or on an assembled flow cell (with an enclosed flow channel).

It is to be understood that terms used herein will take on their ordinary meaning in the relevant art unless specified otherwise. Several terms used herein and their meanings are set forth below.

The singular forms "a", "an", and "the" include plural referents unless the context clearly dictates otherwise.

The terms comprising, including, containing and various forms of these terms are synonymous with each other and are meant to be equally broad.

The terms top, bottom, lower, upper, on, etc. are used herein to describe the flow cell and/or the various components of the flow cell. It is to be understood that these directional terms are not meant to imply a specific orientation, but are used to designate relative orientation between components. The use of directional terms should not be interpreted to limit the examples disclosed herein to any specific orientation(s).

As used herein, "alkyl" refers to a straight or branched hydrocarbon chain that is fully saturated (i.e., contains no double or triple bonds). The alkyl group may have 1 to 20 carbon atoms. Example alkyl groups include methyl, ethyl, propyl, isopropyl, butyl, isobutyl, tertiary butyl, pentyl, hexyl, and the like. As an example, the designation "C1-4 alkyl" indicates that there are one to four carbon atoms in the alkyl chain, i.e., the alkyl chain is selected from the group consisting of methyl, ethyl, propyl, iso-propyl, n-butyl, isobutyl, sec-butyl, and t-butyl.

As used herein, "alkenyl" refers to a straight or branched hydrocarbon chain containing one or more double bonds. The alkenyl group may have 2 to 20 carbon atoms. Example alkenyl groups include ethenyl, propenyl, butenyl, pentenyl, hexenyl, and the like.

As used herein, "alkyne" or "alkynyl" refers to a straight or branched hydrocarbon chain containing one or more triple bonds. The alkynyl group may have 2 to 20 carbon atoms.

As used herein, "aryl" refers to an aromatic ring or ring system (i.e., two or more fused rings that share two adjacent carbon atoms) containing only carbon in the ring backbone. When the aryl is a ring system, every ring in the system is aromatic. The aryl group may have 6 to 18 carbon atoms. Examples of aryl groups include phenyl, naphthyl, azulenyl, and anthracenyl.

As used herein, the term "attached" refers to the state of two things being joined, fastened, adhered, connected or bound to each other. The attachment may be mechanical, or it may be chemical. For example, a nucleic acid can be chemically attached to a functionalized coating layer by a covalent or non-covalent bond. A covalent bond is characterized by the sharing of pairs of electrons between atoms. A non-covalent bond is a physical bond that does not involve the sharing of pairs of electrons and can include, for example, hydrogen bonds, ionic bonds, van der Waals forces, hydrophilic interactions and hydrophobic interactions.

An "azide" or "azido" functional group refers to $-N_3$.

As used herein, the "bonding region" refers to an area on a substrate that is to be bonded to another material, which may be, as examples, a spacer layer, a lid, another substrate, etc., or combinations thereof (e.g., a spacer layer and a lid). The bond that is formed at the bonding region may be a chemical bond (as described above), or a mechanical bond (e.g., using a fastener, etc.).

As used herein, "carbocyclyl" means a non-aromatic cyclic ring or ring system containing only carbon atoms in the ring system backbone. When the carbocyclyl is a ring system, two or more rings may be joined together in a fused, bridged or spiro-connected fashion. Carbocyclyls may have any degree of saturation, provided that at least one ring in a ring system is not aromatic. Thus, carbocyclyls include cycloalkyls, cycloalkenyls, and cycloalkynyls. The carbocyclyl group may have 3 to 20 carbon atoms. Examples of carbocyclyl rings include cyclopropyl, cyclobutyl, cyclopentyl, cyclohexyl, cyclohexenyl, 2,3-dihydro-indene, bicyclo[2.2.2]octanyl, adamantyl, and spiro[4.4]nonanyl.

As used herein, the term "carboxylic acid" or "carboxyl" as used herein refers to $-C(O)OH$.

As used herein, "cycloalkylene" means a fully saturated carbocyclyl ring or ring system that is attached to the rest of the molecule via two points of attachment.

As used herein, "cycloalkenyl" or "cycloalkene" means a carbocyclyl ring or ring system having at least one double bond, wherein no ring in the ring system is aromatic. Examples include cyclohexenyl or cyclohexene and norbornenyl or norbornene. Also as used herein, "heterocycloalkenyl" or "heterocycloalkene" means a carbocyclyl ring or ring system with at least one heteroatom in ring backbone, having at least one double bond, wherein no ring in the ring system is aromatic.

As used herein, "cycloalkynyl" or "cycloalkyne" means a carbocyclyl ring or ring system having at least one triple bond, wherein no ring in the ring system is aromatic. An example is cyclooctyne. Another example is bicyclononyne. Also as used herein, "heterocycloalkynyl" or "heterocycloalkyne" means a carbocyclyl ring or ring system with at least one heteroatom in ring backbone, having at least one triple bond, wherein no ring in the ring system is aromatic.

The term "depositing," as used herein, refers to any suitable application technique, which may be manual or automated, and results in modification of the surface properties. Generally, depositing may be performed using vapor deposition techniques, coating techniques, grafting techniques, or the like. Some specific examples include chemical vapor deposition (CVD), spray coating (e.g., ultrasonic spray coating), spin coating, dunk or dip coating, doctor blade coating, puddle dispensing, flow through coating, aerosol printing, inkjet printing, or the like.

As used herein, the term "depression" refers to a discrete concave feature in a patterned substrate having a surface opening that is completely surrounded by interstitial region(s) of the patterned substrate surface. Depressions can have any of a variety of shapes at their opening in a surface including, as examples, round, elliptical, square, polygonal, star shaped (with any number of vertices), etc. The cross-section of a depression taken orthogonally with the surface can be curved, square, polygonal, hyperbolic, conical, angular, etc. As an example, the depression can be a well.

The term "each," when used in reference to a collection of items, is intended to identify an individual item in the collection but does not necessarily refer to every item in the collection. Exceptions can occur if explicit disclosure or context clearly dictates otherwise.

As used herein, the term "flow cell" is intended to mean a vessel having a chamber (i.e., flow channel) where a reaction can be carried out, an inlet for delivering reagent(s) to the chamber, and an outlet for removing reagent(s) from the chamber. In some examples, the chamber enables the detection of the reaction that occurs in the chamber. For example, the chamber can include one or more transparent surfaces allowing for the optical detection of arrays, optically labeled molecules, or the like, in the chamber.

As used herein, a "flow channel" may be an area defined between two bonded components, which can selectively receive a liquid sample. In some examples, the flow channel may be defined between a patterned substrate and a lid, and thus may be in fluid communication with one or more depressions defined in the patterned substrate.

The "functionalized coating layer" referred to herein is intended to mean a semi-rigid material that is permeable to liquids and gases. The functionalized coating layer may be a hydrogel that can swell when liquid is taken up and that can contract when liquid is removed by drying. In the examples disclosed herein, the functionalized coating layer includes an azide/azido functional group that can react with an alkyne functional group. In an example, the functionalized coating layer is poly(N-(5-azidoacetamidylpentyl) acrylamide-co-acrylamide) (PAZAM).

As used herein, "heteroaryl" refers to an aromatic ring or ring system (e.g., two or more fused rings that share two adjacent atoms) that contain(s) one or more heteroatoms, that is, an element other than carbon, including but not limited to, nitrogen, oxygen and sulfur, in the ring backbone. When the heteroaryl is a ring system, every ring in the system is aromatic. The heteroaryl group may have 5-18 ring members.

As used herein, "heterocyclyl" means a non-aromatic cyclic ring or ring system containing at least one heteroatom in the ring backbone. Heterocyclyls may be joined together in a fused, bridged, or spiro-connected fashion. Heterocyclyls may have any degree of saturation provided that at least one ring in the ring system is not aromatic. In the ring system, the heteroatom(s) may be present in either a non-aromatic or aromatic ring. The heterocyclyl group may have 3 to 20 ring members (i.e., the number of atoms making up the ring backbone, including carbon atoms and heteroatoms). In some examples, the heteroatom(s) are O, N, or S.

The term "hydrazine" or "hydrazinyl" as used herein refers to a -NHNH$_2$ group.

As used herein, the term "hydrazone" or "hydrazonyl" as used herein refers to a

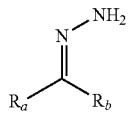

group in which R$_a$ and R$_b$ are defined herein.

A "hydrogel," as used herein, refers to a three-dimensional polymer network structure composed of crosslinked polymer chains. The hydrogel is not water soluble or removable in the liquids to which it is exposed during sequencing.

As used herein, "hydroxy" or "hydroxyl" refers to an —OH group.

As used herein, the term "interstitial region" refers to an area in a substrate or on a surface that separates depressions. For example, an interstitial region can separate one feature of an array from another feature of the array. The two features that are separated from each other can be discrete, i.e., lacking physical contact with each other. In another example, an interstitial region can separate a first portion of a feature from a second portion of a feature. In many examples, the interstitial region is continuous whereas the features are discrete, for example, as is the case for a plurality of wells defined in an otherwise continuous surface. The separation provided by an interstitial region can be partial or full separation. Interstitial regions may have a surface material that differs from the surface material of the features defined in the surface. For example, features of an array can have an amount or concentration of the coating layer and primer(s) that exceeds the amount or concentration present at the interstitial regions. In some examples, the coating layer and primer(s) may not be present at the interstitial regions.

"Nitrile oxide," as used herein, means a "R$_a$C≡N$^+$O$^-$" group in which R$_a$ is defined herein. Examples of preparing nitrile oxide include in situ generation from aldoximes by treatment with chloramide-T or through action of base on imidoyl chlorides [RC(Cl)=NOH].

"Nitrone," as used herein, means a

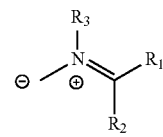

group in which R$_1$, R$_2$, and R$_3$ may be any of the R$_a$ and R$_b$ groups defined herein.

As used herein, a "nucleotide" includes a nitrogen containing heterocyclic base, a sugar, and one or more phosphate groups. Nucleotides are monomeric units of a nucleic acid sequence. In RNA, the sugar is a ribose, and in DNA, the sugar is a deoxyribose, i.e. a sugar lacking a hydroxyl group that is present at the 2' position in ribose. The nitrogen containing heterocyclic base (i.e., nucleobase) can be a purine base or a pyrimidine base. Purine bases include adenine (A) and guanine (G), and modified derivatives or analogs thereof. Pyrimidine bases include cytosine (C), thymine (T), and uracil (U), and modified derivatives or analogs thereof. The C-1 atom of deoxyribose is bonded to N-1 of a pyrimidine or N-9 of a purine.

The term "flow cell substrate" or "substrate" refers to a support upon which the surface chemistry may be added. The term "patterned substrate" refers to a support in which or on which depressions are defined. The substrate may be a wafer, a panel, a rectangular sheet, a die, or any other suitable configuration. The substrate is generally rigid and is insoluble in an aqueous liquid. The substrate may be inert to a chemistry that is used to modify the depressions. For example, a substrate can be inert to chemistry used to apply the functionalized coating layer, to attach the primer(s) to the functionalized coating layer, to apply the hydrogel, etc. Examples of suitable substrates include epoxy siloxane, polyhedral oligomeric silsequioxanes (POSS) or derivatives thereof, glass and modified or functionalized glass, plastics (including acrylics, polystyrene and copolymers of styrene and other materials, polypropylene, polyethylene, polybutylene, polyurethanes, polytetrafluoroethylene (such as TEFLON® from Chemours), cyclic olefins/cyclo-olefin polymers (COP) (such as ZEONOR® from Zeon), polyimides, etc.), nylon, ceramics/ceramic oxides, silica, fused silica, or silica-based materials (e.g., including at least 10% silica), aluminum silicate, silicon and modified silicon (e.g., boron doped p+ silicon), silicon nitride ($Si_3N_4$), silicon oxide ($SiO_2$), tantalum pentoxide ($TaO_5$) or other tantalum oxide(s) ($TaO_x$), hafnium oxide ($HaO_2$), carbon, metals, inorganic glasses, or the like. The substrate may also be glass or silicon or POSS or a derivative thereof, with a coating layer of tantalum oxide or another ceramic oxide at the surface.

As used herein, "plasma ashing" refers to a process of removing organic matter from a substrate by an oxygen plasma. The products that result from plasma ashing may be removed with a vacuum pump/system. Plasma ashing can activate the substrate by introducing reactive hydroxyl groups or carboxyl groups.

As used herein, the "primer" is defined as a single stranded nucleic acid sequence (e.g., single strand DNA or single strand RNA) that serves as a starting point for DNA or RNA synthesis. The 5' terminus of the primer may be modified to allow a coupling reaction with the functionalized coating layer. The primer length can be any number of bases long and can include a variety of non-natural nucleotides. In an example, the sequencing primer is a short strand, ranging from 20 to 40 bases.

As used herein, the terms "silane" and "silane derivative" refer to an organic or inorganic compound containing one or more silicon atoms. An example of an inorganic silane compound is $SiH_4$, or halogenated $SiH_4$ where hydrogen is replaced by one or more halogen atoms. An example of an organic silane compound is $X-R^B-Si(OR^C)_3$, wherein X is an organic group, such as amino, vinyl, methacrylate, epoxy

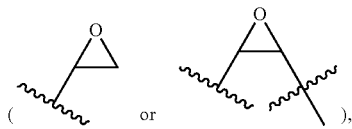

sulfur, alkyl, alkenyl, or alkynyl; $R^B$ is a spacer, for example $-(CH_2)_n-$, wherein n is 0 to 1000; $R^C$ is selected from hydrogen, optionally substituted alkyl, optionally substituted alkenyl, optionally substituted alkynyl, optionally substituted carbocyclyl, optionally substituted aryl, optionally substituted 5-10 membered heteroaryl, and optionally substituted 5-10 membered heterocyclyl, as defined herein. As used herein, the terms "silane" and "silane derivative" can include mixtures of different silane and/or silane derivative compounds.

In some examples, the silane or silane derivative includes an unsaturated moiety that is capable of reacting with a functional group of the functionalized polymer layer. As used herein, the term "unsaturated moiety" refers to a chemical group which includes alkenes, alkynes, cycloalkenes, cycloalkynes, heterocycloalkenes, heterocycloalkynes, or optionally substituted variants thereof including at least one double bond or one triple bond. The unsaturated moieties can be mono-valent or di-valent. When the unsaturated moiety is mono-valent, cycloalkene, cycloalkyne, heterocycloalkene, and heterocycloalkyne are used interchangeably with cycloalkenyls, cycloalkynyls, heterocycloalkenyl, and heterocycloalkynyl, respectively. When the unsaturated moiety is di-valent, cycloalkene, cycloalkyne, heterocycloalkene, and heterocycloalkyne are used interchangeably with cycloalkenylene, cycloalkynylene, heterocycloalkenylene, and heterocycloalkynylene, respectively.

The unsaturated moiety can be covalently attached either directly to the silicon atoms of the silane or silane derivative, or indirectly attached via linkers. Examples of suitable linkers include optionally substituted alkylenes (e.g., bivalent saturated aliphatic radicals (such as ethylene) regarded as being derived from an alkene by opening of the double bond or from an alkane by removal of two hydrogen atoms from different carbon atoms), substituted polyethylene glycols, or the like.

A "spacer layer," as used herein refers to a material that bonds two components together. In some examples, the spacer layer can be a radiation-absorbing material that aids in bonding or can be put into contact with a radiation-absorbing material that aids in bonding.

The term "surface chemistry," as used herein refers to chemically and/or biologically active component(s) that are incorporated into the depressions of the patterned substrate. Examples of the surface chemistry disclosed herein include the functionalized polymer layer attached to at least a portion of a surface of the substrate and/or and the primer attached to at least a portion of the functionalized polymer layer.

A "thiol" functional group refers to —SH.

As used herein, the terms "tetrazine" and "tetrazinyl" refer to six-membered heteroaryl group comprising four nitrogen atoms. Tetrazine can be optionally substituted.

"Tetrazole," as used herein, refer to five-membered heterocyclic group including four nitrogen atoms. Tetrazole can be optionally substituted.

An example of the method 100 is depicted in FIG. 1. The method 100 includes applying a functionalized coating layer in depressions of a patterned flow cell substrate, wherein the depressions are separated by interstitial regions (as shown at reference numeral 102), grafting a primer to the functionalized coating layer to form a grafted functionalized coating layer in the depressions (as shown at reference numeral 104), and applying a hydrogel on at least the grafted functionalized coating layer (as shown at reference numeral 106).

The patterned flow cell substrate may be a patterned wafer or a patterned die or any of the other patterned substrates disclosed herein. Any example of the substrate described herein may be used. The patterned substrate (shown as at reference numeral 12 in FIGS. 3A and 4) includes depressions defined on or in an exposed layer or surface of the substrate, and interstitial regions separating adjacent depressions. The depressions may be fabricated in or on the substrate using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the substrate. Many different layouts of the depressions may be envisaged, as is discussed below in reference to FIG. 4A.

While not shown in FIG. 1, prior to applying the functionalized coating layer and grafting the primer (i.e., prior to adding the surface chemistry), the method may involve treating the surface by exposing the patterned substrate to a cleaning process and/or to another process that prepares the surface (e.g., depressions and, in some instances, adjacent interstitial regions) of the patterned substrate for the subsequent deposition of the surface chemistry. As an example, the method may involve treating the surface of the patterned flow cell substrate to attach a functional group to the surface to form treated depressions and, in some instances, treated interstitial regions. More detailed examples of the treatment process (e.g., the cleaning process and the surface preparation process(es)) are discussed further below in reference to FIGS. 3A through 3I.

In the example shown in FIG. 1, adding the surface chemistry involves applying the functionalized coating layer in the depression(s) (reference numeral 102) and grafting the primer to the functionalized coating layer (reference numeral 104).

An example of the functionalized coating layer includes an acrylamide copolymer, such as poly(N-(5-azidoacetamidylpentyl)acrylamide-co-acrylamide, PAZAM. PAZAM and some other forms of the acrylamide copolymer are represented by Formula (I):

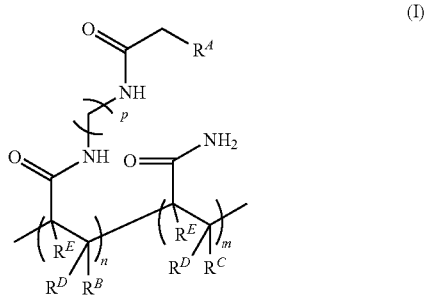

(I)

wherein:
$R^A$ is selected from the group consisting of azido, optionally substituted amino, optionally substituted alkenyl, optionally substituted hydrazone, optionally substituted hydrazine, carboxyl, hydroxy, optionally substituted tetrazole, optionally substituted tetrazine, nitrile oxide, nitrone, and thiol;
$R^B$ is H or optionally substituted alkyl;
$R^C$, $R^D$, and $R^E$ are independently selected from the group consisting of H and optionally substituted alkyl;
each of the —$(CH_2)_p$— can be optionally substituted;
p is an integer in the range of 1 to 50;
n is an integer in the range of 1 to 50,000; and
m is an integer in the range of 1 to 100,000.

One of ordinary skill in the art will recognize that the arrangement of the recurring "n" and "m" features in Formula (I) are representative, and the monomeric subunits may be present in any order in the polymer structure (e.g., random, block, patterned, or a combination thereof).

One specific example of PAZAM are represented by:

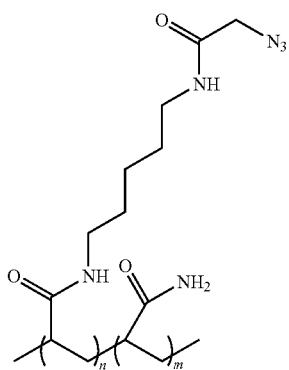

wherein n is an integer in the range of 1-20,000, and m is an integer in the range of 1-100,000.

The molecular weight of the PAZAM may range from about 10 kDa to about 1500 kDa, or may be, in a specific example, about 312 kDa.

In some examples, PAZAM is a linear polymer. In some other examples, PAZAM is a lightly cross-linked polymer.

In other examples, the functionalized coating layer may be a variation of the Formula (I). In one example, the acrylamide unit may be replaced with N,N-dimethylacrylamide

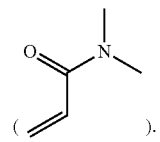

In this example, the acrylamide unit in Formula (I) may be replaced with

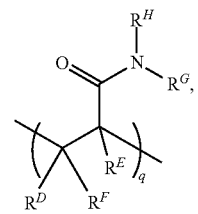

$R^D$, $R^E$, and $R^F$ are each H, and $R^G$ and $R^H$ are each a methyl group (instead of H as is the case with the acrylamide). In this example, q may be an integer in the range of 1 to 100,000. In another example, the N,N-dimethylacrylamide may be used in addition to the acrylamide unit. In this example, Formula (I) may include

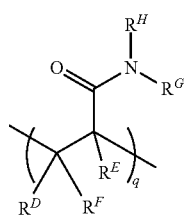

in addition to the recurring "n" and "m" features, where $R^D$, $R^E$, and $R^F$ are each H, and $R^G$ and $R^H$ are each a methyl group. In this example, q may be an integer in the range of 1 to 100,000.

It is to be understood that other functionalized molecules may be used to form the functionalized coating layer, as long as they are functionalized to interact with the patterned substrate and the subsequently applied primer(s). Other examples of suitable molecules for forming the functionalized coating layer include those having a colloidal structure, such as agarose; or a polymer mesh structure, such as gelatin; or a cross-linked polymer structure, such as polyacrylamide polymers and copolymers, silane free acrylamide (SFA), or an azidolyzed version of SFA. Examples of suitable polyacrylamide polymers may be synthesized from acrylamide and an acrylic acid or an acrylic acid containing a vinyl group, or from monomers that form [2+2] photo-cycloaddition reactions.

The functionalized molecule (e.g., PAZAM) may be deposited on the surface of the patterned substrate using spin coating, or dipping or dip coating, or flow of the functionalized molecule under positive or negative pressure, or another suitable technique. The functionalized molecule may be present in a mixture. In an example, the mixture includes PAZAM in water or in an ethanol and water mixture.

After being coated, the functionalized molecule may also be exposed to a curing process to form the functionalized coating layer across the entire patterned substrate (i.e., on depression(s) and interstitial region(s)). In an example, curing the functionalized molecule may take place at a temperature ranging from room temperature (e.g., about 25° C.) to about 60° C. for a time ranging from about 5 minutes to about 2 hours.

To form the functionalized coating layer in the depression(s) and not on the interstitial region(s) of the patterned substrate, the functionalized coating layer may be polished off of the interstitial regions using i) a basic, aqueous slurry having a pH ranging from about 7.5 to about 11 and including an abrasive particle or ii) a polishing pad and a solution free of the abrasive particle.

In this example of the method 100, the primer is then grafted to the functionalized coating layer remaining in the depression(s), as shown at reference numeral 104, to form a grafted functionalized coating layer. Examples of suitable primers include forward amplification primers or reverse amplification primers. Specific examples of suitable primers include P5 or P7 primers, which are used on the surface of commercial flow cells sold by Illumina Inc. for sequencing on HISEQ®, HISEQX®, MISEQ™, MISEQX™, NEXTSEQ™, NOVASEQ™ GENOME ANALYZER™, and other instrument platforms.

Grafting may be accomplished by dunk coating, spray coating, puddle dispensing, or by another suitable method that will attach the primer(s) to the functionalized coating layer in at least some of the depressions. Each of these example techniques may utilize a primer solution or mixture, which may include the primer(s), water, a buffer, and a catalyst.

Dunk coating may involve submerging the patterned substrate (having the functionalized coating layer in the depression(s) thereof) into a series of temperature controlled baths. The baths may also be flow controlled and/or covered with a nitrogen blanket. The baths may include the primer solution or mixture. Throughout the various baths, the primer(s) will attach to the functionalized coating layer in at least some of the depression(s). In an example, the coated and polished patterned substrate will be introduced into a first bath including the primer solution or mixture where a reaction takes place to attach the primer(s), and then the patterned substrate will be moved to additional baths for washing. The patterned substrate may be moved from bath to bath with a robotic arm or manually. A drying system may also be used in dunk coating.

Spray coating may be accomplished by spraying the primer solution or mixture directly onto the coated and polished patterned substrate. The spray coated wafer may be incubated for a time ranging from about 4 minutes to about 60 minutes at a temperature ranging from about 0° C. to about 70° C. After incubation, the primer solution or mixture may be diluted and removed using, for example, a spin coater.

Puddle dispensing may be performed according to a pool and spin off method, and thus may be accomplished with a spin coater. The primer solution or mixture may be applied (manually or via an automated process) to the coated and polished patterned substrate. The applied primer solution or mixture may be applied to or spread across the entire surface of the coated and polished patterned substrate. The primer coated patterned substrate may be incubated for a time ranging from about 2 minutes to about 60 minutes at a temperature ranging from about 0° C. to about 80° C. After incubation, the primer solution or mixture may be diluted and removed using, for example, the spin coater.

In one example, after the primer is grafted to the functionalized coating layer in the depression(s) to form the grafted functionalized coating layer, this example of the method 100 further includes applying the hydrogel on the grafted functionalized coating layer (as shown at reference numeral 106).

The hydrogel may be any hydrophilic polymer that serves as a filter of the sequencing templates that are exposed to the flow cell. The deposition of the hydrogel is controlled in part by the polymer concentration in solution that is deposited on the flow cell. The hydrogel slows down the diffusion of the sequencing templates into the depressions, and thus allows time for a single sequencing template to seed and cluster in a depression before another sequencing template is able to diffuse through the hydrogel. The hydrogel also remains on the flow cell during the sequencing template seeding and during other sequencing steps, and thus is not water soluble or removable in the liquids to which it is exposed during sequencing. Some examples of the hydrogel include PAZAM (or variations thereof as described herein), crosslinked polyacrylamide, an agarose gel, crosslinked polyethylene glycol (PEG), or the like. The hydrogel may be other acrylamide based copolymers, agarose based copolymers, or PEG based copolymers. It is to be understood that an X-based copolymer (e.g., acrylamide based, agarose based, PEG based, etc.) includes the X component in an amount of about 10% or more of the molecular weight composition. In some examples, the X-based copolymer includes about 10% of the molecular weight composition, or about 11% of the molecular weight composition, or about 12% of the molecular weight composition, or about 15% of the molecular weight composition, or about 20% of the molecular weight composition, or about 39% of the molecular weight composition, or a higher percentage of the X component. Moreover, the X component may be higher or lower than the given percentages, as long as the copolymer functions as a hydrogel. A crosslinked PEG hydrogel may be synthesized via covalent cross-linking of PEG macromers with reactive chain ends, such as acrylate, methacrylate, allyl ether, maleimide, vinyl sulfone, NHS ester and vinyl ether groups. Any of the example hydrogels may include hydrophobic or hydrophilic sidechains.

The hydrogel is not grafted with primer(s), but rather coats the primer(s).

In some examples, the hydrogel may be selectively deposited, or patterned, such that the surface chemistry (in this example the functionalized coating layer and the primer(s) thereon) is covered and such that a bonding region of the patterned flow cell substrate remains exposed. The bonding region of the patterned flow cell substrate is generally located on some of the interstitial region(s) of the patterned flow cell substrate where a lid will be bonded to the patterned substrate. When the patterned substrate is a wafer, the bonding region may define the boundaries (e.g., perimeters) of several flow cells that are being formed from the wafer. When the patterned substrate is a die, the bonding region may define the outer boundaries (e.g., perimeter) of one flow cell that is being formed. It is to be understood that other portion(s) of the patterned flow cell substrate that are not part of the bonding region may be coated with the hydrogel.

In this example of the method 100, selectively depositing or patterning the hydrogel may be accomplished via solution incubation, dip coating, spin coating, spray coating, ultrasonic spray coating, doctor blade coating, aerosol printing, or inkjet printing. A mask may be used to cover the bonding region of the patterned substrate so that the hydrogel is not applied on the bonding region. Selective deposition of the hydrogel may be used to deposit the hydrogel on the grafted functionalized coating layer in the depressions, and not on the interstitial regions.

In other examples, the lid may be bonded to the bonding region of the patterned flow cell substrate after the functionalized coating layer is formed, and both the primers and the hydrogel may be applied using flow through processes.

Each of the example techniques for applying the hydrogel may utilize an aqueous mixture, which may include the water and up to about 0.1% (mass to volume) of a hydrogel material. In some examples, the hydrogel material makes up 0.1% or less of the aqueous mixture. In other examples, the aqueous mixture includes from about 0.001% to about 0.1% of the hydrogel material, or from about 0.025% to about 0.005% of the hydrogel material. It is to be understood that the concentration of the aqueous mixture may vary depending upon the flow cell architecture (e.g., the dimensions of the flow channel, input and output ports, etc.). For example, when flow through deposition is utilized, the concentration may be selected so that the aqueous mixture can flow through the flow cell without clogging the port(s), flow channel, etc. As such, the concentration may also be greater than about 0.1%. The hydrogel material (and the resulting hydrogel coating) may be any of the examples disclosed herein (i.e., PAZAM or variations thereof, crosslinked polyacrylamide, an agarose gel, etc.).

In some examples, the aqueous mixture may also include additives, such as co-solvents, antioxidants, dyes, ultraviolet light stabilizers, processing aids, or the like. These additives may be included in the aqueous mixture in amounts that do not deleteriously affect the flowability of the mixture or the film forming ability of the hydrogel.

After the aqueous mixture is applied, it is allowed to incubate to form the hydrogel. The time and temperature for solution incubation may be any time and temperature that is sufficient for hydrogel formation. As examples, the temperature may range from room temperature to about 65° C. and the time may range from about 5 minutes to about 1 hour, or longer. In an example, solution incubation takes place at a temperature of about 50° C. for about 10 minutes.

In some instances, the aqueous mixture may be partially dried during hydrogel formation. Partial drying may be accomplished via air exposure, nitrogen exposure, vacuum, heating (e.g., in an oven), or spin coating (i.e., spinning until dry). In an example in which heating is used, the temperature may be about 50° C., and the hydrogel may be maintained at this temperature for about 10 minutes. The hydrogel may also be washed with a dilute buffer.

Figure 2:
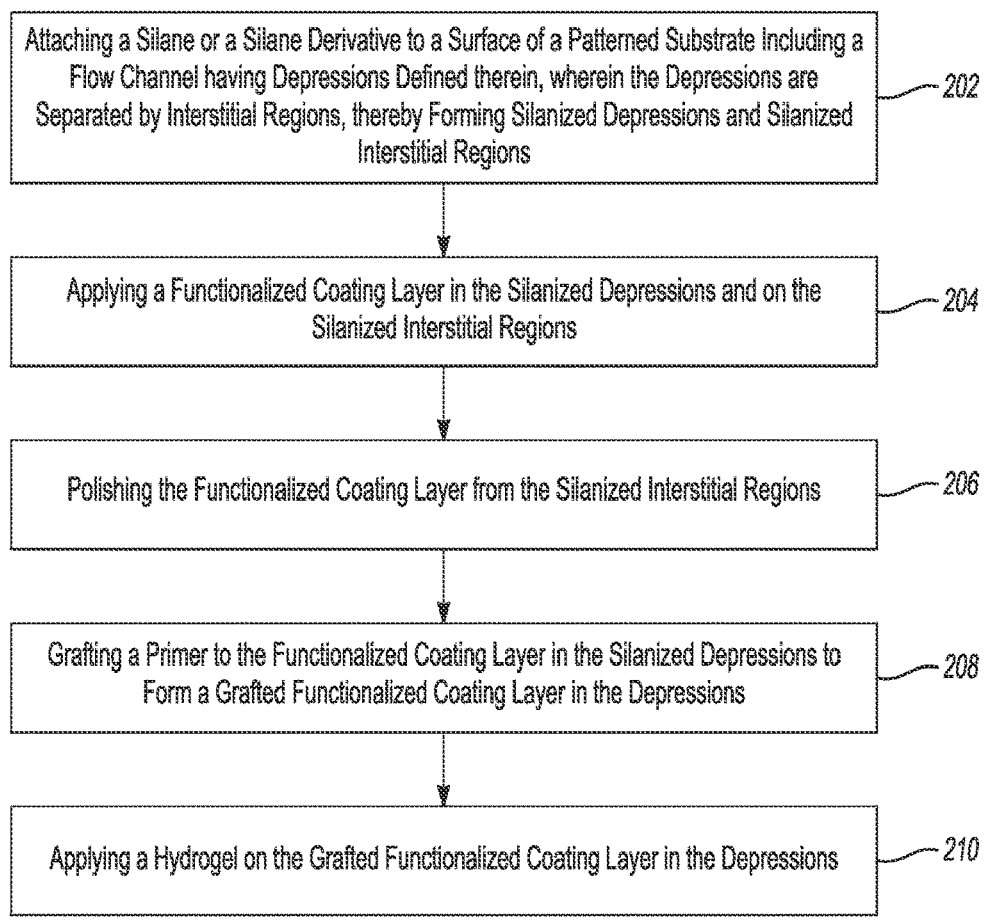
FIG. 2 is a flow diagram illustrating another example of the method disclosed herein.

Another example of the method 200 is depicted in FIG. 2. The method 200 includes attaching a silane or a silane derivative to a surface of a patterned substrate including a flow channel having depressions defined therein, wherein the depressions are separated by interstitial regions, thereby forming silanized depressions and silanized interstitial regions (reference numeral 202), applying a functionalized coating layer in the silanized depressions and on the silanized interstitial regions (reference numeral 204); polishing the functionalized coating layer from the silanized interstitial regions (reference numeral 206); grafting a primer to the functionalized coating layer in the silanized depressions to form a grafted functionalized coating layer in the depressions (reference numeral 208); and applying a hydrogel on the grafted functionalized coating layer in the depressions (reference numeral 210). Examples of the method 200 will be further described in references to FIGS. 3A through 3E, and in FIGS. 3A through 3D in combination with FIGS. 3H and 3I.

Figure 3A:
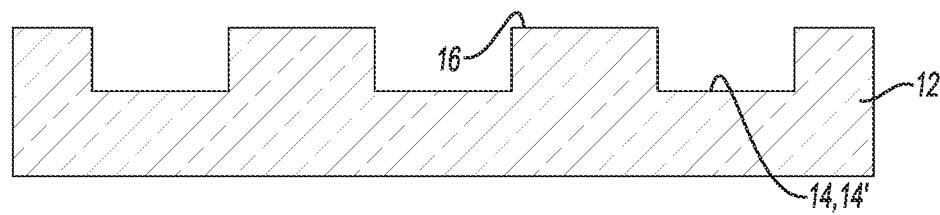
FIGS. 3A through 3G and FIGS. 3A through 3D, 3H and 3I are schematic cross-sectional views depicting respective examples of the method disclosed herein.

FIG. 3A is a cross-sectional view of an example of the patterned substrate 12. The patterned substrate 12 may be a patterned wafer or a patterned die or any other patterned substrate (e.g., panel, rectangular sheet, etc.). Any example of the substrate 12 described herein may be used. The patterned wafer may be used to form several flow cells, and the patterned die may be used to form a single flow cell. In an example, the substrate may have a diameter ranging from about 2 mm to about 300 mm, or a rectangular sheet or panel having its largest dimension up to 10 feet (~3 meters). In an example, the substrate wafer has a diameter ranging from about 200 mm to about 300 mm. In another example, the substrate die has a width ranging from about 0.1 mm to about 10 mm. While example dimensions have been provided, it is to be understood that substrates with any suitable dimensions may be used.

The patterned substrate 12 includes depressions 14 defined on or in an exposed layer or surface of the substrate 12, and interstitial regions 16 separating adjacent depressions 14. In the examples disclosed herein, the depressions 14 become functionalized with surface chemistry (e.g., 20, 22), while the interstitial regions 16 may be used for bonding but will not have primer(s) (22 shown in FIGS. 3E-3G and 3I) present thereon.

The depressions 14 may be fabricated in or on the substrate 12 using a variety of techniques, including, for example, photolithography, nanoimprint lithography, stamping techniques, embossing techniques, molding techniques, microetching techniques, printing techniques, etc. As will be appreciated by those in the art, the technique used will depend on the composition and shape of the substrate 12.

Many different layouts of the depressions 14 may be envisaged, including regular, repeating, and non-regular patterns. In an example, the depressions 14 are disposed in a hexagonal grid for close packing and improved density. Other layouts may include, for example, rectilinear (i.e., rectangular) layouts, triangular layouts, and so forth. In some examples, the layout or pattern can be an x-y format of depressions 14 that are in rows and columns. In some other examples, the layout or pattern can be a repeating arrangement of depressions 14 and/or interstitial regions 16. In still other examples, the layout or pattern can be a random arrangement of depressions 14 and/or interstitial regions 16. The pattern may include spots, pads, wells, posts, stripes, swirls, lines, triangles, rectangles, circles, arcs, checks, plaids, diagonals, arrows, squares, and/or cross-hatches.

The layout or pattern may be characterized with respect to the density of the depressions 14 (i.e., number of depressions 14) in a defined area. For example, the depressions 14 may be present at a density of approximately 2 million per $mm^2$. The density may be tuned to different densities including, for example, a density of at least about 100 per $mm^2$, about 1,000 per $mm^2$, about 0.1 million per $mm^2$, about 1 million per $mm^2$, about 2 million per $mm^2$, about 5 million per $mm^2$, about 10 million per $mm^2$, about 50 million per $mm^2$, or more. Alternatively or additionally, the density may be tuned to be no more than about 50 million per $mm^2$, about 10 million per mm², about 5 million per mm², about 2 million per mm², about 1 million per mm², about 0.1 million per mm², about 1,000 per mm², about 100 per mm², or less. It is to be further understood that the density of depressions 14 on the substrate 12 can be between one of the lower values and one of the upper values selected from the ranges above. As examples, a high density array may be characterized as having depressions 14 separated by less than about 100 nm, a medium density array may be characterized as having depressions 14 separated by about 400 nm to about 1 µm, and a low density array may be characterized as having depressions 14 separated by greater than about 1 µm. While example densities have been provided, it is to be understood that substrates with any suitable densities may be used.

The layout or pattern may also or alternatively be characterized in terms of the average pitch, i.e., the spacing from the center of the depression 14 to the center of an adjacent interstitial region 16 (center-to-center spacing). The pattern can be regular, such that the coefficient of variation around the average pitch is small, or the pattern can be non-regular in which case the coefficient of variation can be relatively large. In either case, the average pitch can be, for example, at least about 10 nm, about 0.1 about 0.5 about 1 about 5 about 10 about 100 or more. Alternatively or additionally, the average pitch can be, for example, at most about 100 about 10 about 5 about 1 about 0.5 about 0.1 or less. The average pitch for a particular pattern of sites 16 can be between one of the lower values and one of the upper values selected from the ranges above. In an example, the depressions 14 have a pitch (center-to-center spacing) of about 1.5 While example average pitch values have been provided, it is to be understood that other average pitch values may be used.

In the examples shown in FIGS. 3A through 3I, the depressions 14 are wells 14', and thus the patterned substrate 12 includes an array of wells 14' in a surface thereof. The wells 14' may be micro wells or nanowells. The size of each well 14' may ach well 14' may be characterized by its volume, well opening area, depth, and/or diameter.

Each well 14' can have any volume that is capable of confining a liquid. The minimum or maximum volume can be selected, for example, to accommodate the throughput (e.g., multiplexity), resolution, analyte composition, or analyte reactivity expected for downstream uses of the flow cell. For example, the volume can be at least about $1 \times 10^{-3}$ µm³, about $1 \times 10^{-2}$ µm³, about 0.1 µm³, about 1 µm³, about 10 µm³, about 100 µm³, or more. Alternatively or additionally, the volume can be at most about $1 \times 10^4$ µm³, about $1 \times 10^3$ µm³, about 100 µm³, about 10 µm³, about 1 µm³, about 0.1 µm³, or less. It is to be understood that the functionalized coating layer can fill all or part of the volume of a well 14'. The volume of the coating layer in an individual well 14' can be greater than, less than or between the values specified above.

The area occupied by each well opening on a surface can be selected based upon similar criteria as those set forth above for well volume. For example, the area for each well opening on a surface can be at least about $1 \times 10^{-3}$ µm², about $1 \times 10^{-2}$ µm², about 0.1 µm², about 1 µm², about 10 µm², about 100 µm², or more. Alternatively or additionally, the area can be at most about $1 \times 10^3$ µm², about 100 µm², about 10 µm², about 1 µm², about 0.1 µm², about $1 \times 10^{-2}$ µm², or less. The area occupied by each well opening can be greater than, less than or between the values specified above.

The depth of each well 14' can be at least about 0.1 µm, about 1 µm, about 10 µm, about 100 µm, or more. Alternatively or additionally, the depth can be at most about $1 \times 10^3$ µm, about 100 µm, about 10 µm, about 1 µm, about 0.1 µm, or less. The depth of each well 14' can be greater than, less than or between the values specified above.

In some instances, the diameter of each well 14' can be at least about 50 nm, about 0.1 µm, about 0.5 µm, about 1 µm, about 10 µm, about 100 µm, or more. Alternatively or additionally, the diameter can be at most about $1 \times 0^3$ µm, about 100 µm, about 10 µm, about 1 µm, about 0.5 µm, about 0.1 µm, or less (e.g., about 50 nm). The diameter of each well 14' can be greater than, less than or between the values specified above.

The patterned substrate 12 may be exposed to a series of processes in order to add the surface chemistry 20, 22 in the depression(s) 14.

While not shown, it is to be understood that the patterned substrate 12 may be exposed to a plasma ashing in order to clean and activate the surface. For example, the plasma ashing process may remove organic material and introduce surface hydroxyl groups. Other suitable cleaning processes may be used to clean the substrate 12, depending, in part, on the type of substrate 12. For example, chemical cleaning may be performed with oxidizing agents or caustic solutions.

Figure 3B:
Figure 3B:
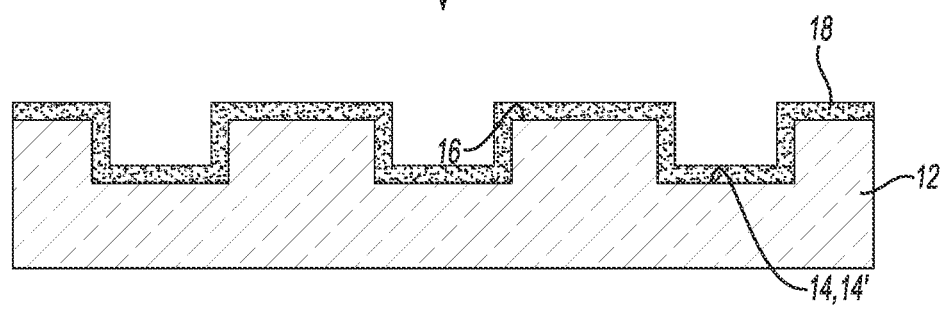
Figure 3C:
Figure 3C:
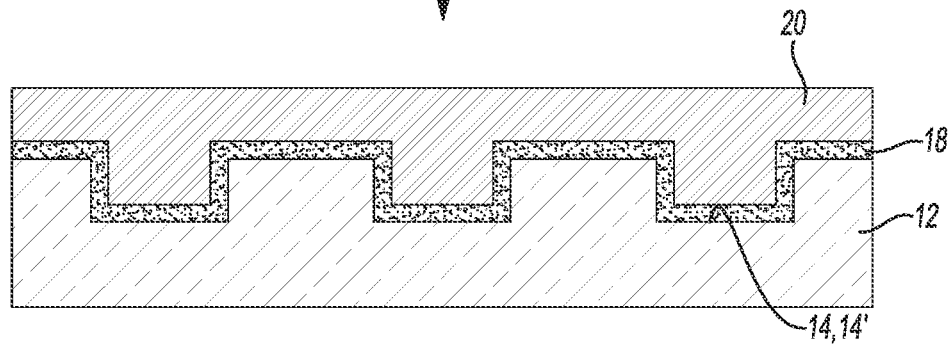

The patterned substrate 12 (shown in FIG. 3A) may then be exposed to a process that will prepare the surface 12 for deposition of the functionalized polymer to form the functionalized polymer layer 20 (FIG. 3C). In an example, the patterned substrate 12 may be exposed to silanization, which attaches a silane or the silane derivative 18 (FIG. 3B) to the patterned wafer surface. Silanization introduces the silane or the silane derivative 18 across the surface, including in the depression 14, 14' (e.g., on the bottom surface and along the side walls) and on the interstitial regions 16. In some aspects, the silane or silane derivative is selectively introduced only to the depressions of a patterned substrate or to micro-locations (which are isolated from each other) of a non-patterned substrate.

Silanization may be accomplished using any silane or silane derivative 18. The selection of the silane or silane derivative 18 may depend, in part, upon the functionalized molecule that is to be used to form the functionalized polymer layer 20 (shown in FIG. 3C), as it may be desirable to form a covalent bond between the silane or silane derivative 18 and the functionalized polymer layer 20. The method used to attach the silane or silane derivative 18 to the substrate 12 may vary depending upon the silane or silane derivative 18 that is being used. Several examples are set forth herein.

In an example, the silane or silane derivative 18 is (3-aminopropyl)triethoxysilane (APTES) or (3-aminopropyl)trimethoxysilane (APTMS) (i.e., X—$R^B$—Si(OR$^C$)$_3$, wherein X is amino, $R^B$ is —(CH$_2$)$_3$—, and $R^C$ is ethyl or methyl). In this example, the substrate 12 surface may be pre-treated with the (3-aminopropyl)triethoxysilane (APTES) or (3-aminopropyl)trimethoxysilane (APTMS) to covalently link silicon to one or more oxygen atoms on the surface (without intending to be held by mechanism, each silicon may bond to one, two or three oxygen atoms). This chemically treated surface is baked to form an amine group monolayer. The amine groups are then reacted with Sulfo-HSAB to form an azido derivative. UV activation at 21° C. with 1 J/cm² to 30 J/cm² of energy generates an active nitrene species, which can readily undergo a variety of insertion reactions with PAZAM (e.g., the functionalized molecule). In some aspects, a silane or silane derivative is selectively applied to the depressions of a patterned substrate or to micro-locations on a non-patterned substrate.

Other silanization methods may also be used. Examples of suitable silanization methods include vapor deposition, a YES method, spin coating, or other deposition methods. Some examples of methods and materials that may be used to silanize the substrate 12 are described herein, although it is to be understood that other methods and materials may be used.

In an example utilizing the YES CVD oven, the patterned substrate 12 is placed in the CVD oven. The chamber may be vented and then the silanization cycle started. During cycling, the silane or silane derivative vessel may be maintained at a suitable temperature (e.g., about 120° C. for norbornene silane), the silane or silane derivative vapor lines be maintained at a suitable temperature (e.g., about 125° C. for norbornene silane), and the vacuum lines be maintained at a suitable temperature (e.g., about 145° C.).

In another example, the silane or silane derivative 18 (e.g., liquid norbornene silane) may be deposited inside a glass vial and placed inside a glass vacuum desiccator with a patterned substrate 12. The desiccator can then be evacuated to a pressure ranging from about 15 mTorr to about 30 mTorr, and placed inside an oven at a temperature ranging from about 60° C. to about 125° C. Silanization is allowed to proceed, and then the desiccator is removed from the oven, cooled and vented in air.

Vapor deposition, the YES method and/or the vacuum desiccator may be used with a variety of silane or silane derivative 18, such as those silane or silane derivatives 18 including examples of the unsaturated moieties disclosed herein. As examples, these methods may be used when the silane or silane derivative 18 includes an alkene or cycloalkene unsaturated moiety, such as norbornene, a norbornene derivative (e.g., a (hetero)norbornene including an oxygen or nitrogen in place of one of the carbon atoms), transcyclooctene, transcyclooctene derivatives, transcyclopentene, transcycloheptene, trans-cyclononene, bicyclo[3.3.1]non-1-ene, bicyclo[4.3.1]dec-1 (9)-ene, bicyclo [4.2.1]non-1(8)-ene, and bicyclo[4.2.1]non-1-ene. Any of these cycloalkenes can be substituted, for example, with an R group, such as hydrogen, alkyl, alkenyl, alkynyl, cycloalkyl, cycloalkenyl, cycloalkynyl, aryl, heteroaryl, heteroalicyclyl, aralkyl, or (heteroalicyclyl)alkyl. An example of the norbornene derivative includes [(5-bicyclo[2.2.1]hept-2-enyl)ethyl] trimethoxysilane. As other examples, these methods may be used when the silane or silane derivative 18 includes an alkyne or cycloalkyne unsaturated moiety, such as cyclooctyne, a cyclooctyne derivative, or bicyclononynes (e.g., bicyclo[6.1.0]non-4-yne or derivatives thereof, bicyclo [6.1.0]non-2-yne, or bicyclo[6.1.0]non-3-yne). These cycloalkynes can be substituted with any of the R groups described herein.

As shown in FIG. 3B, the attachment of the silane or silane derivative 18 forms a silanized patterned substrate, including silanized depressions and silanized interstitial regions (which are one example of the treated depressions and treated interstitial regions).

The silanized patterned wafer may then be exposed to a process that will form the functionalized polymer layer 20 on the silanized depressions and silanized interstitial regions.

As described herein, examples of the functionalized polymer layer 20 include PAZAM, or any other molecule that is functionalized to interact with the patterned wafer 12 and the subsequently applied primer(s) 22. The functionalized molecule may be present in a mixture. In an example, the mixture includes PAZAM in water, or in an ethanol and water mixture. The functionalized polymer layer 20 may be formed on the surface of the silanized patterned wafer (i.e., onto the silanized depressions and the silanized interstitial regions) using any suitable technique. The functionalized molecule may be deposited on the surface of the patterned substrate 12 using spin coating, or dipping or dip coating, or flow of the functionalized molecule under positive or negative pressure, or other suitable techniques. The resulting layer 20 is shown in FIG. 3C.

The attachment of the functionalized polymer layer 20 to the silanized depressions and silanized interstitial regions (i.e., 18) may be through covalent bonding. The covalent linking of the functionalized polymer layer 20 to the silanized depressions is helpful for maintaining the functionalized polymer layer 20 in the depressions 14, 14' throughout the lifetime of the ultimately formed flow cell during a variety of uses. The following are some examples of reactions that can take place between the silane or silane derivative 18 and the functionalized polymer layer 20.

When the silane or silane derivative 18 includes norbornene or a norbornene derivative as the unsaturated moiety, the norbornene or a norbornene derivative can: i) undergo a 1,3-dipolar cycloaddition reaction with an azide/azido group of PAZAM; ii) undergo a coupling reaction with a tetrazine group attached to PAZAM; iii) undergo a cycloaddition reaction with a hydrazone group attached to PAZAM; iv) undergo a photo-click reaction with a tetrazole group attached to PAZAM; or v) undergo a cycloaddition with a nitrile oxide group attached to PAZAM.

When the silane or silane derivative 18 includes cyclooctyne or a cyclooctyne derivative as the unsaturated moiety, the cyclooctyne or cyclooctyne derivative can: i) undergo a strain-promoted azide-alkyne 1,3-cycloaddition (SPAAC) reaction with an azide/azido of PAZAM, or ii) undergo a strain-promoted alkyne-nitrile oxide cycloaddition reaction with a nitrile oxide group attached to PAZAM.

When the silane or silane derivative 18 includes a bicyclononyne as the unsaturated moiety, the bicyclononyne can undergo similar SPAAC alkyne cycloaddition with azides or nitrile oxides attached to PAZAM due to the strain in the bicyclic ring system.

While not shown, it is to be understood that in some examples of the method, the patterned substrate 12 may not be exposed to silanization. Rather, the patterned substrate 12 may be exposed to plasma ashing, and then the functionalized polymer layer 20 may be directly spin coated (or otherwise deposited) on the plasma ashed patterned substrate 12. In this example, plasma ashing may generate surface-activating agent(s) (e.g., -OH groups) that can adhere the functionalized coating layer 20 to the patterned substrate 12. In these examples, the functionalized polymer layer 20 is selected so that it reacts with the surface groups generated by plasma ashing.

After being coated, the functionalized molecule may also be exposed to a curing process to form the functionalized polymer layer 20 across the entire patterned substrate (i.e., on depression(s) 14 and interstitial region(s) 16). In an example, curing the functionalized molecule may take place at a temperature ranging from room temperature (e.g., about 25° C.) to about 95° C. for a time ranging from about 1 millisecond to about several days. In another example, the time may range from 10 seconds to at least 24 hours. In still another example, the time may range from about 5 minutes to about 2 hours.

The silanized and coated patterned substrate (shown in FIG. 3C) may be exposed to a cleaning process. This process may utilize a water bath and sonication. The water bath may be maintained at a relatively low temperature ranging from about 22° C. to about 45° C. In another example the water bath temperature ranges from about 25° C. to about 30° C.

Figure 3D:
Figure 3D:
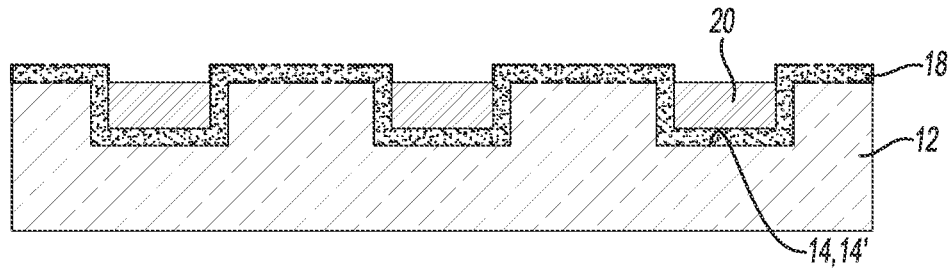

The silanized and coated patterned substrate is then exposed to polishing, if needed, to remove portion(s) of the functionalized polymer layer 20 from the silanized interstitial regions. The silanized, coated, and polished patterned substrate is shown in FIG. 3D. The portions of the silane or silane derivative 18 that are adjacent to the interstitial regions 16 may or may not be removed as a result of polishing. As such, in FIGS. 3D through 3I, the portions of the silane or silane derivative 18 that are adjacent to the interstitial regions 16 are shown in phantom, as they may at least partially remain after polishing or they may be removed after polishing. When these silanized portions are completely removed, it is to be understood that the underlying substrate 12 is exposed.

The polishing process may be performed with a gentle chemical slurry (including, e.g., an abrasive, a buffer, a chelating agent, a surfactant, and/or a dispersant) which can remove the thin functionalized polymer layer 20, and in some instances, at least part of the silane or silane derivative 18, from the interstitial regions 16 without deleteriously affecting the underlying substrate 12 at those regions. Alternatively, polishing may be performed with a solution that does not include the abrasive particles.

The chemical slurry may be used in a chemical mechanical polishing system to polish the surface of the silanized and coated patterned substrate shown in FIG. 3C. The polishing head(s)/pad(s) or other polishing tool(s) is/are capable of polishing the functionalized polymer layer 20 from the interstitial regions 16 while leaving the functionalized polymer layer 20 in the depressions 14, 14' and leaving the underlying substrate 12 at least substantially intact. As an example, the polishing head may be a Strasbaugh ViPRR II polishing head.

As mentioned above, polishing may be performed with a polishing pad and a solution without any abrasive. For example, the polish pad may be utilized with a solution free of the abrasive particle (i.e., a solution that does not include abrasive particles).

Polishing removes portion(s) of the functionalized polymer layer 20 (and in some instances at least part of the silane or silane derivative 18) from the interstitial regions 16 and leaves portion(s) of the functionalized polymer layer 20 in the silanized depressions, as shown in FIG. 3D. Also as mentioned above, the interstitial region(s) 16 may remain silanized after polishing is complete. In other words, the silanized interstitial regions may remain intact after the polishing. Alternatively (as indicated by the phantom portions of 18), the silane or silane derivative 18 may be removed from the interstitial region(s) 16 as a result of polishing.

While not shown, it is to be understood that the silanized, coated, and polished patterned substrate (shown in FIG. 3D) may be exposed to a cleaning process. This process may utilize a water bath and sonication. The water bath may be maintained at a relatively low temperature ranging from about 22° C. to about 30° C. The silanized, coated, and polished patterned substrate may also be spin dried, or dried via another suitable technique.

Figure 3E:
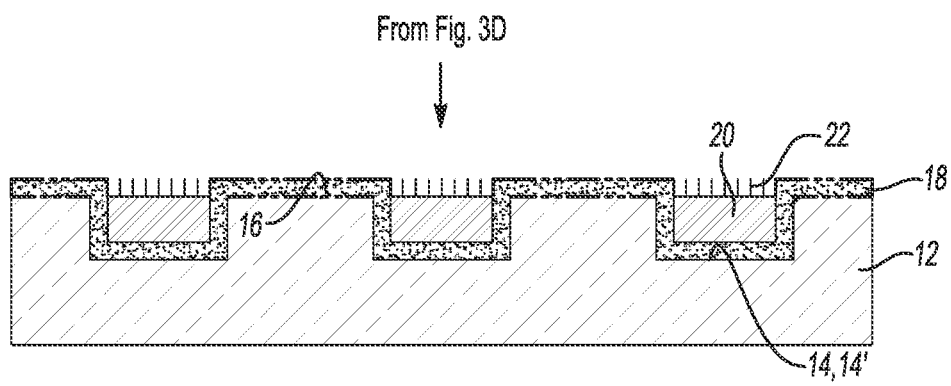
Figure 3F:
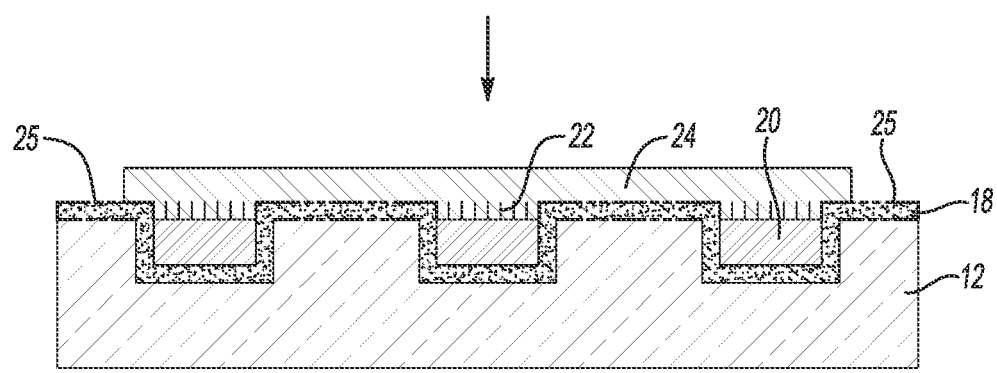
Figure 3G:
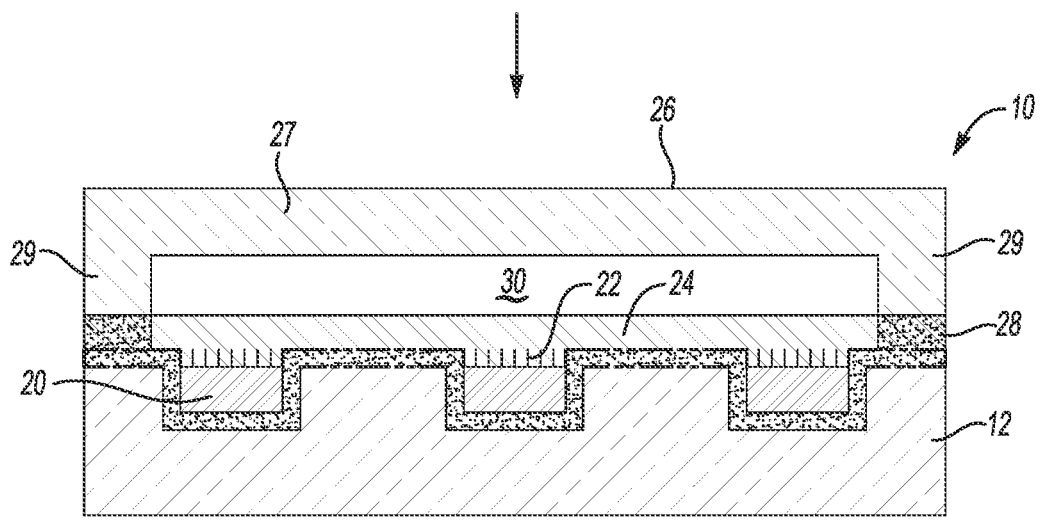
Figure 3H:
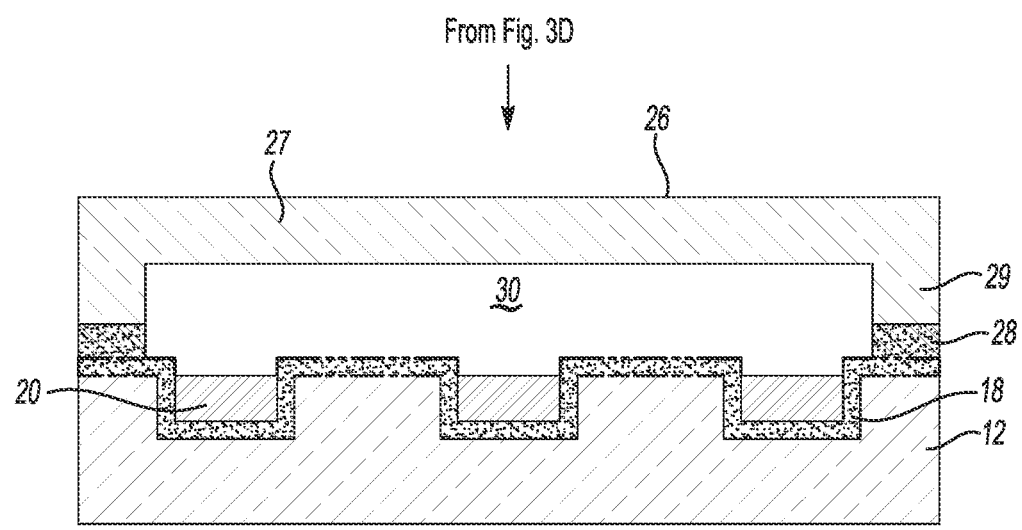
Figure 3I:
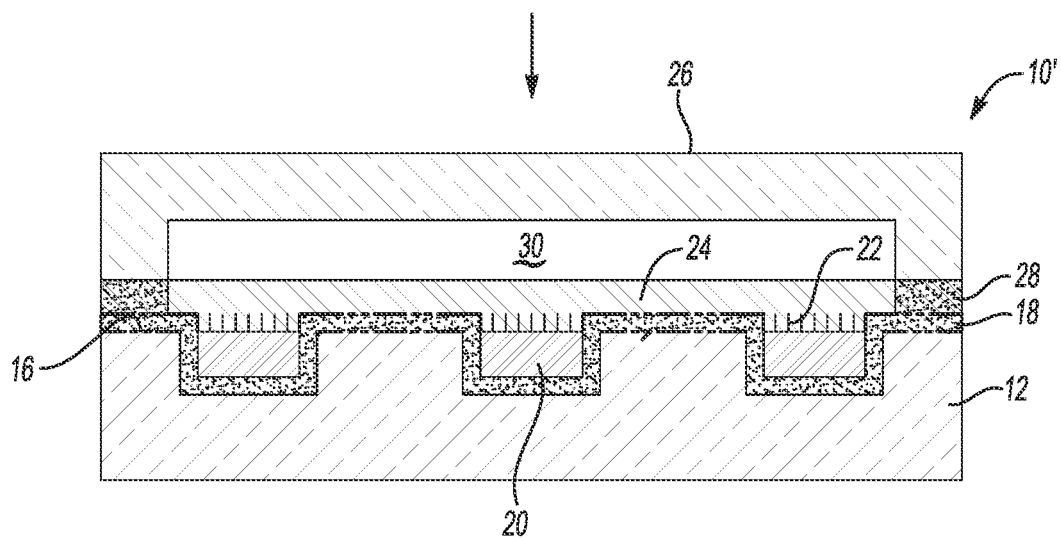

The silanized, coated, and polished patterned substrate shown in FIG. 3D may then be exposed to the processes shown in FIGS. 3E through 3G, which generate the flow cell 10, or to the processes shown in FIGS. 3H through 3I, which generate the flow cell 10'. In FIGS. 3E through 3G, the primers 22 are grafted and the hydrogel 24 is applied before the lid 26 is bonded to the patterned flow cell substrate 12. In FIGS. 3H and 3I, the lid 26 is bonded to the patterned flow cell substrate 12 before the primers 22 are grafted and the hydrogel 24 is applied.

In FIG. 3E, a grafting process is performed in order to graft the primer 22 to the functionalized polymer layer 20 in the depression(s) 14, 14'. In this example, grafting may be accomplished by dunk coating, spray coating, puddle dispensing, or by another suitable method that will attach the primer(s) 22 to the functionalized polymer layer 20 in at least some of the depressions 14, 14'. Each of these example techniques may utilize the primer solution or mixture disclosed herein, which may include the primer(s), water, a buffer, and a catalyst, and may be performed as described herein.

As shown in FIG. 3F, after the primer 22 is grafted to the functionalized coating layer 20 in the depressions 14, 14', the hydrogel 24 is formed on the grafted functionalized coating layer 20, 22 and on at least a portion of the patterned flow cell substrate 12. In this example, the hydrogel 24 may be formed on the exposed surface of the patterned substrate 12 that is not part of a bonding region 25. In this example, the hydrogel 24 is selectively deposited or patterned on the interstitial regions 16 between adjacent depressions 14, 14', but not at the edge/periphery of the patterned substrate 12 where the bonding region 25 is located. The selective deposition/patterning of the hydrogel 24 may be accomplished using the aqueous mixture, as described herein. After the aqueous mixture is deposited, it may be partially dried to form the hydrogel 24.

As depicted in FIG. 3G, the lid 26 may then be bonded to the bonding region 25. When the patterned flow cell substrate 12 is a wafer, different areas of the lid 26 may at least partially define respective flow channels 30 that are being formed using the wafer. When the patterned flow cell substrate 12 is a die, the lid 26 may define the one or more flow channels 30 that is/are being formed.

The lid 26 may be any material that is transparent to an excitation light that is directed toward the surface chemistry 20, 22 in the depression(s) 14. As examples, the lid 26 may be glass (e.g., borosilicate, fused silica, etc.), plastic, or the like. A commercially available example of a suitable borosilicate glass is D 263®, available from Schott North America, Inc. Commercially available examples of suitable plastic materials, namely cyclo olefin polymers, are the ZEONOR® products available from Zeon Chemicals L.P.

In some examples, the lid 26 may be integrally formed with sidewall(s) 29 that correspond with the shape of the bonding region 25, and that will be bonded to the bonding region 25. For example, a recess may be etched into a transparent block to form a substantially planar (e.g., top) portion 27 and sidewall(s) 29 extending from the substantially planar portion 27. When the etched block is mounted to the bonding region of the patterned substrate 12, the recess may become the flow channel 30.

In other examples, the sidewall(s) 29 and the lid 26 may be separate components that are coupled to each other. For example, the lid 26 may be a substantially rectangular block having an at least substantially planar exterior surface and an at least substantially planar interior surface that defines a portion (e.g., a top portion) of the flow channel 30 (once bonded to the patterned substrate 12). The block may be mounted onto (e.g., bonded to) the sidewall(s) 29, which are bonded to the bonding region 25 of the patterned flow cell substrate 12 and form sidewall(s) of the flow channel 30. In this example, the sidewall(s) 29 may include any of the materials set forth herein for the spacer layer (described below).

The lid 26 may be bonded to the bonding region 25 of the patterned flow cell substrate 12 using any suitable technique, such as laser bonding, diffusion bonding, anodic bonding, eutectic bonding, plasma activation bonding, glass frit bonding, or others methods known in the art. In an example, a spacer layer 28 may be used to bond the lid 26 to the bonding region 25. The spacer layer 28 may be any material that will seal at least some of the interstitial regions 16 (e.g., the bonding region 25) of the patterned substrate 12 and the lid 26 together.

In one example, the spacer layer 28 may be a radiation-absorbing material that absorbs radiation at a wavelength that is transmitted by the lid 26 and/or the patterned substrate 12. The absorbed energy, in turn, forms the bond between the spacer layer 28 and the lid 26 and between the spacer layer 28 and the patterned substrate 12. An example of this radiation-absorbing material is black KAPTON® (polyimide containing carbon black) from DuPont (USA), which absorbs at about 1064 nm. It is to be understood that polyimide could be used without the addition of carbon black, except that the wavelength would have to be altered to one that is significantly absorbed by the natural polyimide material (e.g., 480 nm). As another example, polyimide CEN JP can be bonded when irradiated with light at 532 nm. When the spacer layer 28 is the radiation-absorbing material, the spacer layer 28 may be positioned at an interface between the lid 26 and the patterned substrate 12 so that the spacer layer 28 contacts the desired bonding region 25. Compression may be applied (e.g., approximately 100 PSI of pressure) while laser energy at a suitable wavelength is applied to the interface (i.e., the radiation-absorbing material is irradiated). The laser energy may be applied to the interface both from the top and from the bottom in order to achieve suitable bonding.

In another example, the spacer layer 28 may include a radiation-absorbing material in contact therewith. The radiation-absorbing material may be applied at the interface between the spacer layer 28 and the lid 26 as well as at the interface between the spacer layer 28 and the patterned flow cell substrate 12. As an example, the spacer layer 28 may be polyimide and the separate radiation-absorbing material may be carbon black. In this example, the separate radiation-absorbing material absorbs the laser energy that forms the bonds between the spacer layer 28 and the lid 26 and between the spacer layer 28 and the patterned substrate 12. In this example, compression may be applied at the respective interfaces while laser energy at a suitable wavelength is applied to the interfaces (i.e., the radiation-absorbing material is irradiated).

When the patterned flow substrate 12 is a wafer, the spacer layer 28 and sidewalls 29 (of or connected to the lid 26) may physically separate one flow channel 30 from an adjacent flow channel 30 and may be located at the periphery of the wafers. When the patterned substrate 12 is a die and the flow cell 10 that is being formed is to include a single flow channel 30 or lane, the spacer layer 28 and sidewalls 29 (of or connected to the lid 26) may be located at the periphery of the die to define the flow channel 30 and seal the flow cell 10. When the patterned substrate 12 is a die and the flow cell 10 that is being formed is to include multiple isolated flow channels 30 (e.g., eight or four flow channels/lanes), the spacer layer 28 and sidewalls 29 (of or connected to the lid 26) may physically separate one flow channel/lane 30 from an adjacent flow channel/lane 30 and may be located at the periphery of the die. It is to be understood, however, that the spacer layer 28 and sidewalls 29 may be located in any desired region depending on the implementation.

When the patterned substrate 12 is a die, assembling the flow cell 10 may involve the bonding of the lid 26. When the patterned substrate is a wafer, assembling the flow cell 10 may involve additional processing, such as dicing, after the lid 26 is bonded. In one example, the lid 26 may be bonded to the patterned wafer 12 and dicing forms individual flow cells 10. As mentioned herein, on a wafer, the sidewalls 29 may physically separate one flow channel 30 from an adjacent flow channel 30, and thus dicing may take place through at least some of the sidewalls 29, so that each individual flow cell 10 includes a desirable number of flow channels 30, each of which has a portion of the original sidewall 29 surrounding its periphery. In another example, the patterned wafer may be diced to form non-lidded dies, which can have respective lids 26 bonded thereto to form individual flow cells 10.

In the example shown in FIG. 3G, the lid 26 includes the top portion 27 integrally formed with sidewall(s) 29. The sidewall(s) 29 are bonded to the bonding region 25 of the patterned substrate 12 through the spacer layer 28.

Together, the lid 26 and the patterned flow cell substrate 12 define the flow channel 30, which is in selective fluid communication with the depressions 14, 14'. The flow channel 30 may serve to, for example, selectively introduce reaction components or reactants to the hydrogel 24 and the underlying surface chemistry 20, 22 in order initiate designated reactions in/at the depressions 14, 14'.

An example of the flow cell 10 is shown in FIG. 3G.

Referring now to FIGS. 3H and 3I, another example of the method 200 includes bonding the lid 26 to the patterned flow cell substrate 12 before the primers 22 are grafted and the hydrogel 24 is applied.

As shown in FIG. 3H, the functionalized coating layer 20 has been applied (e.g., deposited and polished) as described in FIG. 3D and in reference to FIG. 1. At least some of the polished interstitial regions 16 may define the bonding region 25, and the lid 26 may be bonded to the bonding region 25. The lid 26 may be any of the materials and may have any of the configurations described herein. The lid 26 may be bonded to the bonding region 25 via any of the techniques described herein.

In the example shown in FIG. 3H, the lid 26 includes a top portion 27 integrally formed with sidewall(s) 29. The sidewall(s) 29 are bonded to the bonding region 25 of the patterned substrate 12 through the spacer layer 28. After the lid 26 is bonded, the flow channel 30 is formed between the lid 26 and the patterned substrate 12. The flow channel 30 may serve to selectively introduce various fluids to the flow cell 10' (FIG. 3I).

In this example of the method 200, the primer 22 is then grafted to the functionalized coating layer 20 in the depression(s) 14, as shown in FIG. 3I. Any of the primers described herein may be used. In this example, grafting may be accomplished by a flow through process. In the flow through process, the primer solution or mixture described herein may be introduced into the flow channel(s) 30 through respective input port(s) (not shown), may be maintained in the flow channel(s) 30 for a time sufficient (i.e., an incubation period) for the primer 22 to attach to the functionalized coating layer 20 in one or more of the depressions 14, and then may be removed from respective output port(s) (not shown). After primer 22 attachment, the additional fluid(s) may be directed through the flow channel(s) 30 to wash the now functionalized depressions and the flow channel(s) 30.

After the primer 22 is grafted to the functionalized coating layer 20 in the depression(s) 14, this example of the method 200 further includes forming the hydrogel on the grafted functionalized coating layer 20, 22 and on at least some of the interstitial regions 16 (e.g., those regions 16 between the depressions 14).

In this example, the hydrogel coating 14 may be deposited by a flow through process. In the flow through process, the aqueous mixture (including water and the hydrogel material) may be introduced into the flow channel(s) 30 of the flow cell(s) through respective input port(s) and may be maintained in the flow channel(s) 30. Enough of the aqueous mixture may be introduced to cover the grafted functionalized coating layer 20, 22 and any exposed surfaces of the patterned flow cell substrate 12 within the flow channel 30. This solution incubation forms the hydrogel coating 24. In some examples, while the mixture is in the flow channel(s) 30, the flow channel(s) 30 may be exposed to a dry down process where air, nitrogen, or vacuum is flushed through the input port for a set amount of time to partially dry the hydrogel coating 24 on the surface chemistry 20, 22 and any exposed portions (e.g., some interstitial regions 16) of the substrate 12. In this example, the hydrogel coating 24 may be any of the examples disclosed herein.

Figure 4:
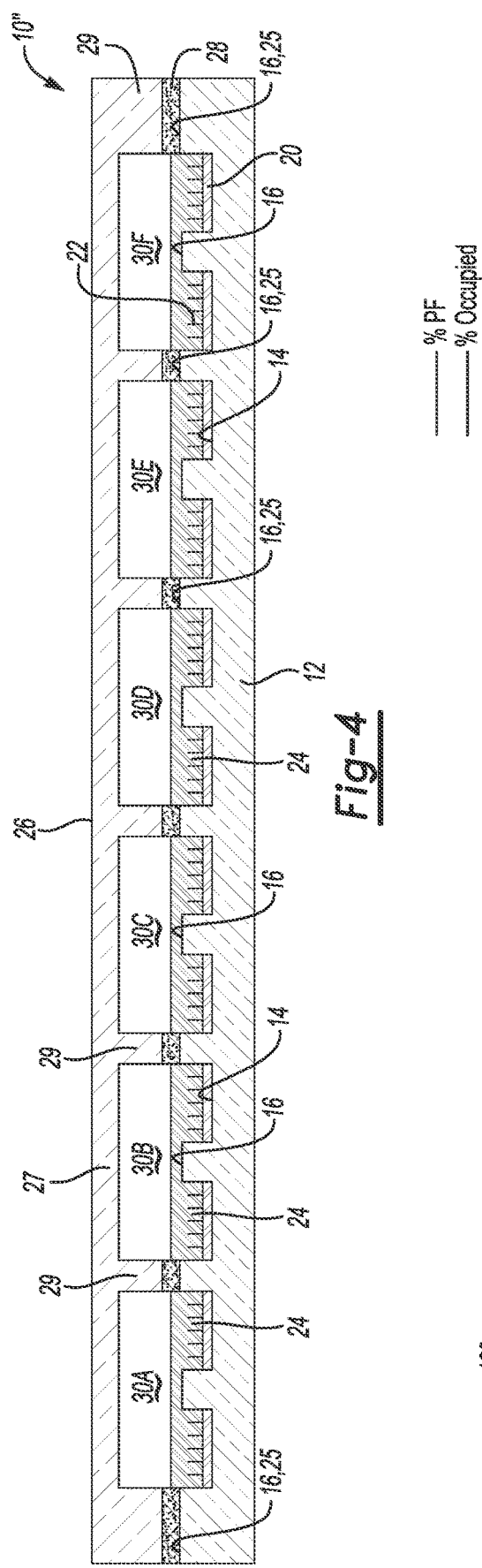
FIG. 4 is a cross-sectional view of an example flow cell formed by the methods shown in FIGS. 3A through 3G and FIGS. 3A through 3D, 3H and 3I.

An example of the flow cell 10" formed by the methods 100, 200 disclosed herein is shown in FIG. 4. The flow cell 10" includes the patterned substrate 12, which may be a die that has been exposed to the processes of the method 100, 200, or a wafer that has been that has been exposed to the processes of the method 100, 200 and has been diced.

Generally, the patterned substrate 12 includes depressions 14 separated by interstitial regions 16, and surface chemistry 20, 22 positioned in the depressions 14. The surface chemistry includes the functionalized coating layer 20 and the primers 22. While not shown, it is to be understood that the depressions 14 may also have surface preparation or treatment chemistry (e.g., silane or a silane derivative) positioned between the substrate 12 and the functionalized coating layer 20. This same surface preparation or treatment chemistry may also be positioned on the interstitial regions 16.

The flow cell 10" also includes the lid 26 bonded to bonding region(s) 25 of the patterned substrate 12, wherein the lid 26 at least partially defines a flow channel 30A, 30B, etc. that is in selective communication with the depressions 14. In the example shown in FIG. 4, the lid 26 includes a top portion 27 that is connected to several sidewalls 29, and these components 27, 29 define a portion of each of the six flow channels 30A, 30B, 30C, 30D, 30E, 30F. The respective sidewalls 29 isolate one flow channel 30A, 30B, 30C, 30D, 30E, 30F from each adjacent flow channel 30A, 30B, 30C, 30D, 30E, 30F, each flow channel 30A, 30B, 30C, 30D, 30E, 30F is in selective fluid communication with a respective set of the depressions 14.

While not shown, the lid 26 or the patterned substrate 12 may include inlet and outlet ports that are to fluidically engage other ports (not shown) for directing fluid(s) into the respective flow channels 30A, 30B, 30C, 30D, 30E, 30F (e.g., from a reagent cartridge or other fluid storage system) and out of the flow channel (e.g., to a waste removal system).

The hydrogel/hydrogel coating 24 covers the surface chemistry 20, 22 in the depressions 14, and at least a portion of the patterned substrate 12 (e.g., those interstitial regions 16 that are not also bonding regions 25). In the example flow cell 10", the hydrogel/hydrogel coating 24 has been formed as described herein. As such, the hydrogel/hydrogel coating 24 may be any of the examples disclosed herein (i.e., PAZAM, crosslinked polyacrylamide, agarose gel, etc.).

While not shown, it is to be understood that some examples of the flow cell 10, 10', 10" may be affixed directly to, and thus be in physical contact with, a detection device (not shown) through one or more securing mechanisms (e.g., adhesive, bond, fasteners, and the like). The detection device may include a CMOS device (which includes a plurality of stacked layers including, for example, silicon layer(s), dielectric layer(s), metal-dielectric layer(s), metal layer(s), etc.) and optical components. The optical components may be arranged such that an optical sensor of the detection device is at least substantially aligned with, and thus is operatively associated with, a single optical waveguide of the detection device and the surface chemistry 20, 22 within a single depression 14, 14' or within a flow channel 30 of the flow cell.

Also while not shown, it is to be understood that instead of being bonded to a lid 26, a functionalized substrate (with surface chemistry, 20, 22 and the hydrogel/hydrogel coating 24 thereon) may be bonded to another functionalized substrate with surface chemistry, 20, 22 and the hydrogel/hydrogel coating 24 thereon. The two functionalized surfaces can face each other and can have a flow channel defined therebetween. A spacer layer and suitable bonding method may be used to bond two of the functionalized substrates together.

The flow cells 10, 10', 10" disclosed herein may be used in a variety of sequencing approaches or technologies, including techniques often referred to as sequencing-by-synthesis (SBS), cyclic-array sequencing, sequencing-by-ligation, pyrosequencing, and so forth. With any of these techniques and in examples using a patterned substrate, since the functional polymer layer 20 and attached sequencing primer(s) 22 are present in the functionalized depressions (i.e., 14, 14' with surface chemistry 20, 22 thereon) and not on the interstitial regions 16, amplification will be confined to the functionalized depressions. Moreover, due to the presence of the hydrogel 24, there is more time (as compared to when the hydrogel is not included) to amplify one sequencing template into larger clusters, which increases the population of depressions 14 across the patterned flow cell substrate 12 that seeds a single sequencing template.

As one example, a sequencing by synthesis (SBS) reaction may be run on a system such as the HISEQ™, HISEQX™, MISEQ™, NOVASEQ™, or NEXTSEQ™ sequencer systems from Illumina, Inc. (San Diego, Calif.). In SBS, extension of a nucleic acid primer (e.g., primer 22) along a nucleic acid template (i.e., the sequencing template) is monitored to determine the sequence of nucleotides in the template. The underlying chemical process can be polymerization (e.g., catalyzed by a polymerase enzyme) or ligation (e.g., catalyzed by a ligase enzyme). In a particular polymerase-based SBS process, fluorescently labeled nucleotides are added to the primer 22 (thereby extending the primer 22) in a template dependent fashion such that detection of the order and type of nucleotides added to the primer 22 can be used to determine the sequence of the template. For example, to initiate a first SBS cycle, one or more labeled nucleotides, DNA polymerase, etc., may be delivered into/through the flow channel 30, etc. that houses an array of primers 22 coated with the hydrogel 24. The functionalized depressions (i.e., 14, 14' with surface chemistry 20, 22 thereon), where primer extension causes a labeled nucleotide to be incorporated, can be detected through an imaging event. During an imaging event, an illumination system (not shown) may provide an excitation light to the functionalized depressions (i.e., 14, 14' with surface chemistry 20, 22 thereon).

In some examples, the nucleotides can further include a reversible termination property that terminates further primer extension once a nucleotide has been added to the primer 22. For example, a nucleotide analog having a reversible terminator moiety can be added to the primer 22 such that subsequent extension cannot occur until a deblocking agent is delivered to remove the moiety. Thus, for examples that use reversible termination, a deblocking reagent can be delivered to the flow channel 30, etc. (before or after detection occurs).

Wash(es) may take place between the various fluid delivery steps. The SBS cycle can then be repeated n times to extend the primer 22 by n nucleotides, thereby detecting a sequence of length n.

While SBS has been described in detail, it is to be understood that the flow cells 10, 10', 10" described herein may be utilized with other sequencing protocol, for genotyping, or in other chemical and/or biological applications.

To further illustrate the present disclosure, examples are given herein. It is to be understood that these examples are provided for illustrative purposes and are not to be construed as limiting the scope of the disclosure.

NON-LIMITING WORKING EXAMPLES

Example 1

A flow cell was used that included 8 flow channels/lanes defined on a patterned fused silica substrate, where each lane included 96 tiles (which correspond with an imaging area), and where each tile was in fluid communication with a plurality of wells. A PAZAM layer was formed in each well, and 1 μm primers were grafted on the PAZAM layer.

Lanes 1-4, and thus tiles 1 to 384, were comparative example lanes and tiles. As such, a hydrogel coating was not applied on the PAZAM layer or the primers in these lanes and tiles. Lanes 5-8, and thus tiles 385 to 768, were example lanes and tiles. As such, a hydrogel coating was applied on the PAZAM layer and on the primers in these lanes and tiles. The hydrogel coating was another PAZAM layer that was applied via the flow through process. A 0.025% PAZAM solution in water was introduced to lanes 5-8, was heated to 60° C., and was maintained at that temperature for about 10 minutes.

All of the lanes were washed with a dilute buffer.

A sequencing cycle was performed in each of the lanes 1-8. A Phi X sequencing template solution having a concentration of 150 pM was used.

Figure 5:
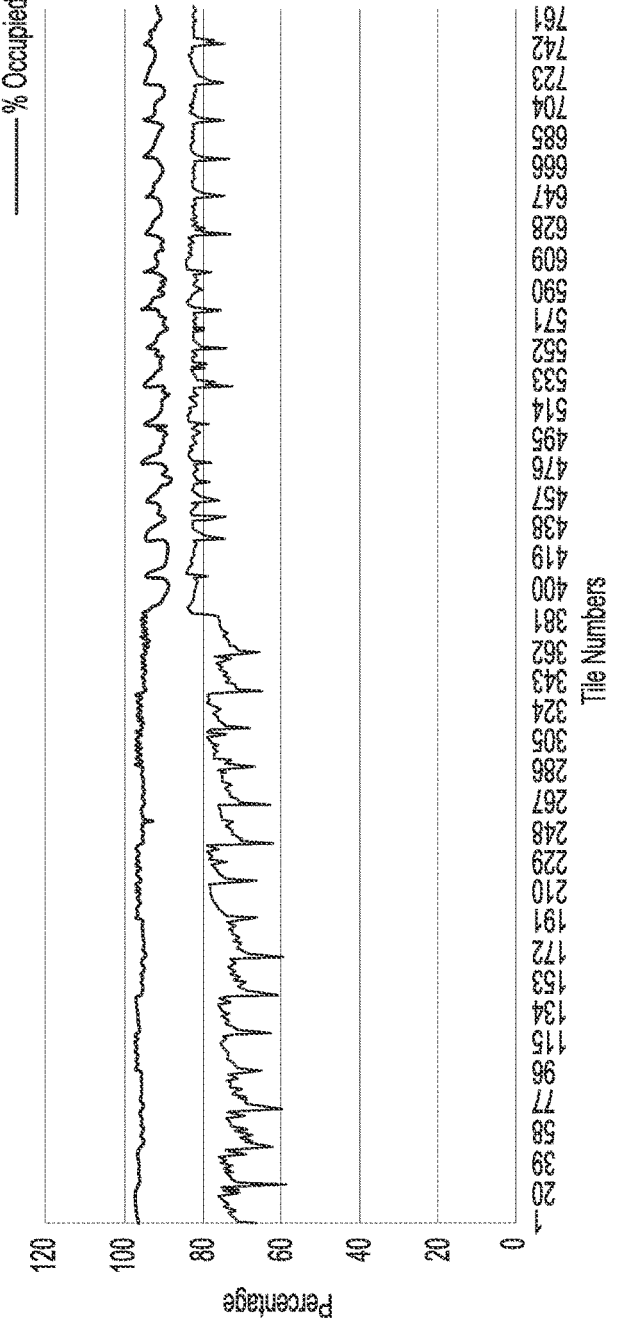
FIG. 5 is a plot illustrating the percentage of clusters passing filter (% PF) and the percentage of depressions/wells occupied with DNA template (% Occupied) for tiles of a comparative flow cell without a hydrogel coating (1-384 on the X-axis) and tiles of an example flow cell including a hydrogel coating (385-768 on the X-axis)

FIG. 5 shows the percentage of clusters passing through a filter (% passing filter (%P F)) and the percentage of wells occupied with the DNA sequencing template (% Occupied). % Passing filter (% PF) is the metric used to describe clusters which pass a chastity threshold and are used for further processing and analysis of sequencing data. Higher % passing filter results in increased yield of unique clusters used for sequencing data.

The data in FIG. 5 shows that the % passing filter was improved (by about 5% to about 10%) when the hydrogel was used (compare the data for tiles 1 through 384 (no hydrogel) to the data for tiles 385 through 768 (with hydrogel).

The difference between the % Occupied and the % PF is a rough estimate of polyclonal clusters. The difference between the % Occupied and the % PF Tiles for example tiles 385 through 768, is much less than the difference between the % Occupied and the % PF Tiles for comparative tiles 1 through 384, which indicates that the PAZAM hydrogel coated tiles/lanes had much less polyclonal clustering than the comparative uncoated tiles/lanes.

Overall, the data in FIG. 5 indicates that the presence of the hydrogel coating helps improve monoclonal clustering and the purity of the major component/cluster in polyclone cluster wells, which would also improve sequencing yield and data quality.

Example 2

Two flow cells were used, each of which included 8 flow channels/lanes defined on a patterned fused silica substrate, where each lane included 96 tiles (and imaging areas), and where each tile was in fluid communication with a plurality of wells. A PAZAM layer was formed in each well, and 1 μm primers were grafted on the PAZAM layer.

In the comparative flow cell, a hydrogel coating was not applied on the PAZAM layer or the primers in any of lanes and tiles.

In the example flow cell, a hydrogel coating was applied on the PAZAM layer and on the primers in each of the lanes and tiles. The hydrogel coating was another PAZAM layer that was applied via the flow through process. A mixture/solution of PAZAM in water was introduced to lanes 1-8 of the example flow cell, was heated to 60° C., and was maintained at that temperature for about 10 minutes.

All of the lanes in the comparative flow cell and the example flow cell were washed with a dilute buffer.

Sequencing cycles were performed in each of the lanes 1-8 of each of the comparative flow cell and the example flow cell. 151 cycles were sequenced in readl, and another 151 cycles were sequenced in read 2. Sequencing metrics were pulled from the center of the tiles, to remove edge effects. Different sequencing template solutions having different concentrations ranging from 100 pM to 800 pM were used in each of the lanes. More specifically, lane 1 of each of the comparative and example flow cells was exposed to a 100 pM sequencing template solution; lane 2 of each of the comparative and example flow cells was exposed to a 200 pM sequencing template solution; lane 3 of each of the comparative and example flow cells was exposed to a 300 pM sequencing template solution; lane 4 of each of the comparative and example flow cells was exposed to a 400 pM sequencing template solution; lane 5 of each of the comparative and example flow cells was exposed to a 500 pM sequencing template solution; lane 6 of each of the comparative and example flow cells was exposed to a 600 pM sequencing template solution; lane 7 of each of the comparative and example flow cells was exposed to a 700 pM sequencing template solution; and lane 8 of each of the comparative and example flow cells was exposed to an 800 pM sequencing template solution.

Figure 6:
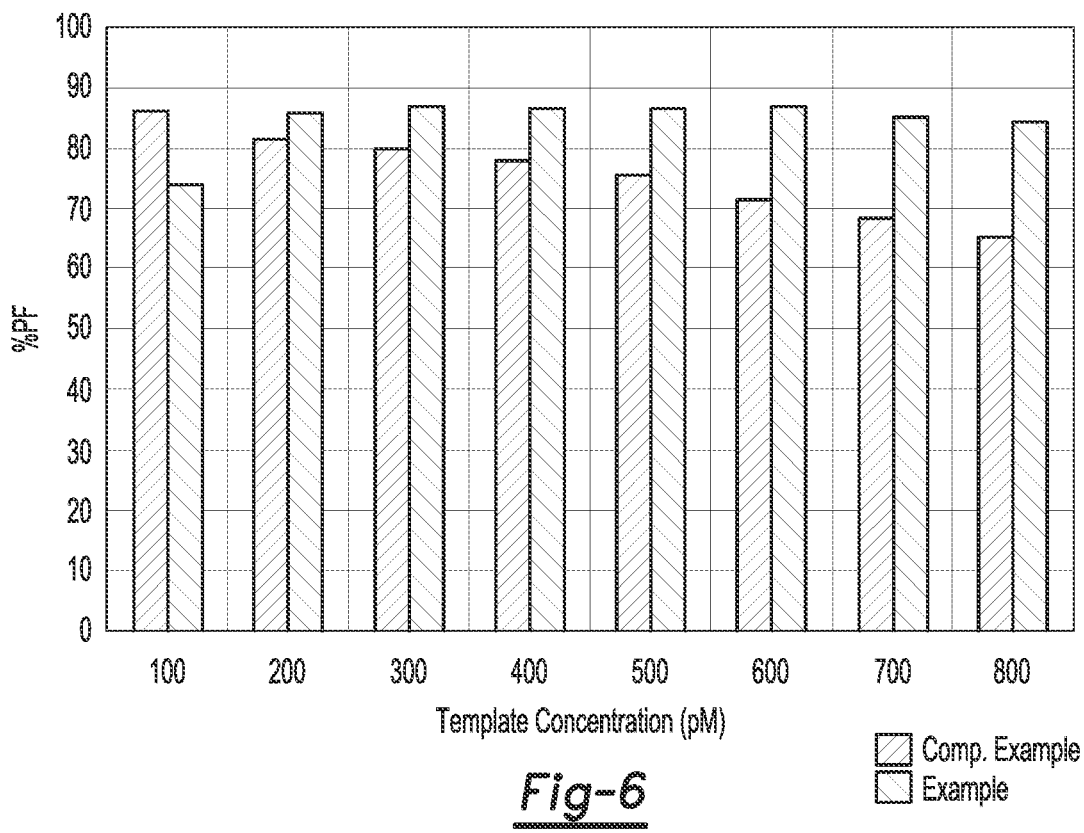
FIG. 6 is a plot of the percentage of clusters passing filter (% PF) versus a template concentration (pM) for a comparative example flow cell and an example flow cell including a hydrogel coating.

FIG. 6 shows the percentage of clusters passing through a filter (% passing filter (% PF) for the various lanes of the comparative example and the example flow cells. As illustrated, the % PF was more consistent for the example flow cell lanes including the hydrogel across a wider concentration range than the comparative flow cell lanes with the hydrogel.

Figure 7:
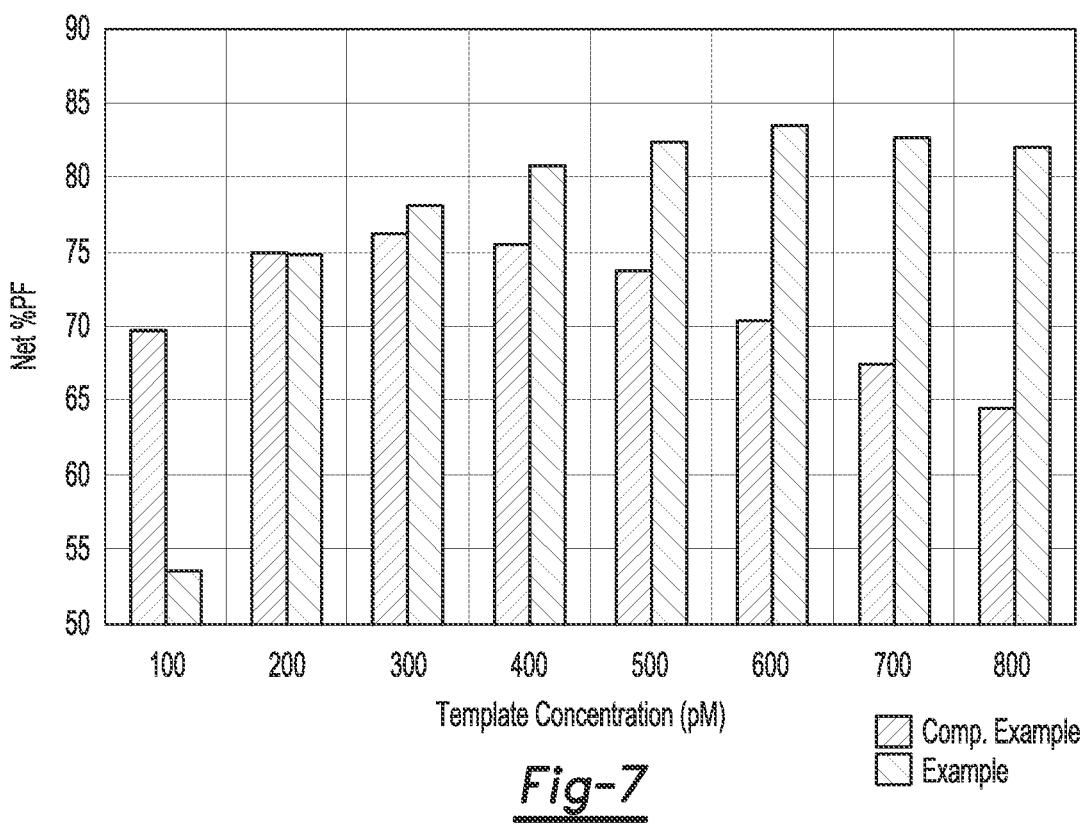
FIG. 7 is a plot of the net percentage of clusters passing filter (% PF) after removing duplicate templates versus a template concentration (pM) for the comparative example flow cell and the example flow cell including the hydrogel coating.

Duplicate templates were removed bioinformatically from the example flow cell lanes and the comparative flow cell lanes, according to if the reads align to the exact same genomic positions. The net % PF after duplicate removal is shown in FIG. 7. Overall, a higher yield (from about 2% to about 17% yield gain) can be obtained with the hydrogel coated flow cell using sequencing templates having a concentration ranging from 300 pM to 800 pM when compared to the comparative flow cell.

The maximum % PF after duplicate removal for the comparative flow cell was 76.13% in the lane exposed to the 300 pM sequencing template solution. The maximum % PF after duplicate removal for the example flow cell was 83.42% in the lane exposed to the 600 pM sequencing template solution. This illustrates a 9.6% gain in monoclonal clusters.

Figure 8B:
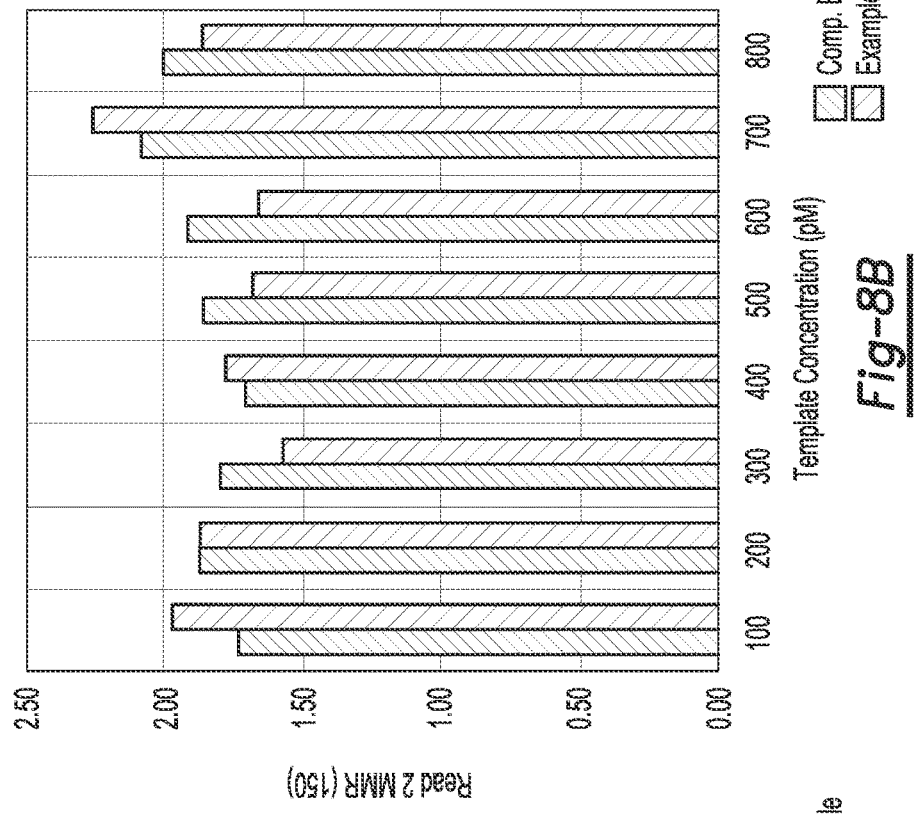
FIGS. 8A and 8B are plot of the read 1 (R1) (FIG. 8A) and the read 2 (R2) (FIG. 8B) mismatch rates after 150 sequencing cycles for the comparative example flow cell and the example flow cell including the hydrogel coating.
Figure 8A:
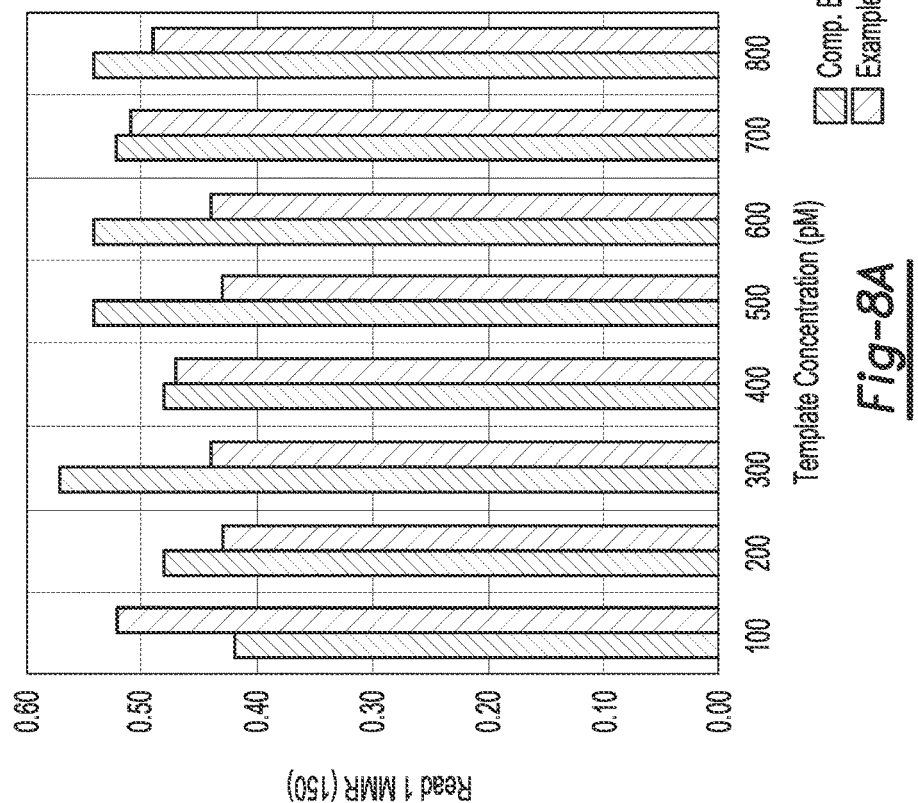

FIGS. 8A and 8B illustrate the read 1 and read 2 mismatch rates (MMR) for the comparative example flow cell and the example flow cell after 150 sequencing cycles. The similar mismatch rates across the comparative and example flow cells indicates that the hydrogel coating does not deleteriously affect the sequencing operation.

Additional Notes

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

It is to be understood that the ranges provided herein include the stated range and any value or sub-range within the stated range. For example, a range from 1 to 50,000, should be interpreted to include not only the explicitly recited limits of from 1 to 50,000, but also to include individual values, such as about 708, about 945 about 3,500, etc., and sub-ranges, such as from about 825 to about 29,000, from about 95 to about 40,000, etc. Furthermore, when "about" and/or "substantially" are/is utilized to describe a value, they are meant to encompass minor variations (up to +/−10%) from the stated value.

While several examples have been described in detail, it is to be understood that the disclosed examples may be modified. Therefore, the foregoing description is to be considered non-limiting.

What is claimed is:

1. A method, comprising:
    applying a functionalized coating layer in depressions of a patterned flow cell substrate, wherein the depressions are separated by interstitial regions and wherein the patterned flow cell substrate includes a bonding region;
    grafting a primer to the functionalized coating layer to form a grafted functionalized coating layer in the depressions;
    applying a non-grafted hydrogel on at least the grafted functionalized coating layer, the non-grafted hydrogel being selected from the group consisting of crosslinked polyacrylamide, an agarose gel, and crosslinked polyethylene glycol; and
    bonding a lid to the patterned flow cell substrate at the bonding region, thereby defining a flow channel between the patterned flow cell substrate and the lid.

2. The method as defined in claim 1, wherein the non-grafted hydrogel is disposed on the grafted functionalized coating layer and on some of the interstitial regions.

3. The method as defined in claim 1, wherein prior to applying the functionalized coating layer, the method further comprises treating a surface of the patterned flow cell substrate to attach a functional group to the surface to form treated depressions and treated interstitial regions.

4. The method as defined in claim 3, wherein applying the functionalized coating layer in the depressions includes:
    applying the functionalized coating layer in the treated depressions and on the treated interstitial regions; and
    polishing the functionalized coating layer from the treated interstitial regions.

5. The method as defined in claim 1, wherein applying the non-grafted hydrogel involves applying an aqueous mixture including from about 0.001% up to about 0.1% (mass to volume) of a hydrogel material.

6. The method as defined in claim 1, wherein the bonding region of the patterned flow cell substrate has a spacer layer bonded thereto, and wherein after the non-grafted hydrogel is applied, the bonding of the lid to the patterned flow cell substrate comprises bonding the lid to the spacer layer.

7. The method as defined in claim 1, wherein applying the non-grafted hydrogel includes selectively depositing the non-grafted hydrogel on the grafted functionalized coating layer.

* * * * *